(12) United States Patent
Pool et al.

(10) Patent No.: US 9,770,274 B2
(45) Date of Patent: Sep. 26, 2017

(54) INTRAMEDULLARY IMPLANTS FOR REPLACING LOST BONE

(71) Applicant: NuVasive Specialized Orthopedics, Inc., San Diego, CA (US)

(72) Inventors: Scott Pool, Laguna Hills, CA (US); Blair Walker, Mission Viejo, CA (US)

(73) Assignee: NuVasive Specialized Orthopedics, Inc., San Diego, CA (US)

( * ) Notice: Subject to any disclaimer, the term of this patent is extended or adjusted under 35 U.S.C. 154(b) by 0 days.

(21) Appl. No.: 15/212,090

(22) Filed: Jul. 15, 2016

(65) Prior Publication Data

US 2017/0035470 A1 Feb. 9, 2017

Related U.S. Application Data

(63) Continuation of application No. 14/451,190, filed on Aug. 4, 2014, now Pat. No. 9,421,046, which is a
(Continued)

(51) Int. Cl.
*A61B 17/56* (2006.01)
*A61B 17/58* (2006.01)
(Continued)

(52) U.S. Cl.
CPC .......... *A61B 17/7216* (2013.01); *A61B 17/84* (2013.01); *A61B 17/846* (2013.01); *A61B 17/86* (2013.01); *A61B 17/8872* (2013.01)

(58) Field of Classification Search
CPC .. A61B 17/72; A61B 17/7216; A61B 17/7225
(Continued)

(56) References Cited

U.S. PATENT DOCUMENTS 5,356,411 A 10/1994 Spievack
5,429,638 A 7/1995 Muschler et al.
(Continued)

FOREIGN PATENT DOCUMENTS

FR 2961386 12/2011

OTHER PUBLICATIONS

Hyodo, A., Kotschi, H., Kambic, H., Muschler, G., "Bone Transport Using Intramedullary Fixation and a Single Flexible Traction Cab;e", Clinical Orthopaedics and Related Research, 1996, No. 325, pp. 256-268.
(Continued)

*Primary Examiner* — Ellen C Hammond
*Assistant Examiner* — Christina Negrellirodrigue
(74) *Attorney, Agent, or Firm* — Jeremy A. Smith; Bradley Arant Boult Cummings LLP

(57) ABSTRACT

A bone transport system includes a nail having a proximal end and a distal end, the proximal end configured for securing to a first portion of bone, the distal end configured for securing to a second portion of bone. The system includes a housing having a wall with a longitudinal opening extending a length along a portion thereof. The system further includes a transport sled having a length that is shorter than the length of the longitudinal opening, the transport sled configured for securing to a third portion of bone, the transport sled further configured to be moveable along the longitudinal opening. The system further includes a magnetic assembly disposed within the nail and configured to be non-invasively actuated by a moving magnetic field, wherein actuation of the magnetic assembly moves the transport sled along the longitudinal opening. The system further includes a ribbon extending on opposing sides of the transport sled and substantially covering the longitudinal opening.

1 Claim, 16 Drawing Sheets

Related U.S. Application Data continuation of application No. 13/655,246, filed on Oct. 18, 2012, now Pat. No. 9,044,281.

(51) Int. Cl.

| | | |
|---|---|---|
| *A61F 2/30* | (2006.01) | |
| *A61B 17/72* | (2006.01) | |
| *A61B 17/84* | (2006.01) | |
| *A61B 17/86* | (2006.01) | |
| *A61B 17/88* | (2006.01) | |

(58) Field of Classification Search
USPC .......... 606/60, 61, 62, 63, 246, 256–258, 90
See application file for complete search history.

(56) References Cited

U.S. PATENT DOCUMENTS

| | | | |
|---|---|---|---|
| 5,626,579 | A | 5/1997 | Muschler et al. |
| 5,976,138 | A | 11/1999 | Baumgart et al. |
| 6,336,929 | B1 * | 1/2002 | Justin ............... A61B 90/98 606/63 |
| 6,375,682 | B1 | 4/2002 | Fleischmann et al. |
| 6,416,516 | B1 | 7/2002 | Stauch et al. |
| 6,706,042 | B2 | 3/2004 | Taylor |
| 7,063,706 | B2 | 6/2006 | Wittenstein |
| 7,357,635 | B2 | 4/2008 | Belfor et al. |
| 7,458,981 | B2 | 12/2008 | Fielding |
| 7,531,002 | B2 | 5/2009 | Sutton et al. |
| 7,601,156 | B2 | 10/2009 | Robinson |
| 7,611,526 | B2 | 11/2009 | Carl et al. |
| 7,666,184 | B2 | 2/2010 | Stauch |
| 7,776,091 | B2 | 8/2010 | Mastrorio et al. |
| 7,794,476 | B2 | 9/2010 | Wisnewski |
| 7,811,328 | B2 | 10/2010 | Molz, IV et al. |
| 7,887,566 | B2 | 2/2011 | Hynes |
| 8,043,299 | B2 | 10/2011 | Conway |
| 8,105,363 | B2 | 1/2012 | Fielding et al. |
| 8,147,517 | B2 | 4/2012 | Trieu et al. |
| 8,147,549 | B2 | 4/2012 | Metcalf et al. |
| 8,177,789 | B2 | 5/2012 | Magill et al. |
| 8,211,179 | B2 | 7/2012 | Molz, IV et al. |
| 8,216,275 | B2 | 7/2012 | Fielding et al. |
| 8,221,420 | B2 | 7/2012 | Keller |
| 8,241,331 | B2 | 8/2012 | Arnin |
| 8,252,063 | B2 | 8/2012 | Stauch |
| 8,282,671 | B2 | 10/2012 | Connor |
| 8,298,240 | B2 | 10/2012 | Giger et al. |
| 8,419,801 | B2 | 4/2013 | DiSilvestro et al. |
| 8,439,915 | B2 | 5/2013 | Harrison et al. |
| 8,469,908 | B2 | 6/2013 | Asfora |
| 8,486,110 | B2 | 7/2013 | Fielding et al. |
| 8,529,606 | B2 | 9/2013 | Alamin et al. |
| 8,562,653 | B2 | 10/2013 | Alamin et al. |
| 8,568,457 | B2 | 10/2013 | Hunziker |
| 8,632,544 | B2 | 1/2014 | Haaja et al. |
| 8,641,723 | B2 | 2/2014 | Connor |
| 8,663,285 | B2 | 3/2014 | Dall et al. |
| 8,777,947 | B2 * | 7/2014 | Zahrly ............... A61B 17/7216 606/62 |
| 8,870,959 | B2 | 10/2014 | Arnin |
| 8,894,663 | B2 | 11/2014 | Giger et al. |
| 8,961,567 | B2 | 2/2015 | Hunziker |
| 8,968,406 | B2 | 3/2015 | Arnin |
| 8,992,527 | B2 | 3/2015 | Guichet |
| 9,022,917 | B2 | 5/2015 | Kasic et al. |
| 9,044,281 | B2 | 6/2015 | Pool et al. |
| 2003/0144669 | A1 | 7/2003 | Robinson |
| 2003/0220644 | A1 | 11/2003 | Thelen et al. |
| 2004/0023623 | A1 | 2/2004 | Stauch et al. |
| 2005/0090823 | A1 | 4/2005 | Bartim |
| 2005/0159754 | A1 | 7/2005 | Odrich |
| 2005/0234448 | A1 | 10/2005 | McCarthy |
| 2006/0235424 | A1 | 10/2006 | Vitale et al. |
| 2006/0293683 | A1 | 12/2006 | Stauch |
| 2007/0010814 | A1 | 1/2007 | Stauch |
| 2007/0264605 | A1 | 11/2007 | Belfor et al. |
| 2008/0108995 | A1 | 5/2008 | Conway et al. |
| 2008/0161933 | A1 | 7/2008 | Grotz et al. |
| 2008/0167685 | A1 | 7/2008 | Allard et al. |
| 2008/0172063 | A1 | 7/2008 | Taylor |
| 2008/0228186 | A1 | 9/2008 | Gall et al. |
| 2008/0255615 | A1 | 10/2008 | Vittur et al. |
| 2009/0062798 | A1 | 3/2009 | Conway |
| 2009/0076597 | A1 | 3/2009 | Dahlgren et al. |
| 2009/0093890 | A1 | 4/2009 | Gelbart |
| 2009/0171356 | A1 | 7/2009 | Klett |
| 2009/0192514 | A1 | 7/2009 | Feinberg et al. |
| 2009/0254088 | A1 | 10/2009 | Soubeiran |
| 2009/0281542 | A1 | 11/2009 | Justis |
| 2009/0318919 | A1 | 12/2009 | Robinson |
| 2010/0100185 | A1 | 4/2010 | Trieu et al. |
| 2010/0249847 | A1 | 9/2010 | Jung et al. |
| 2011/0057756 | A1 | 3/2011 | Marinescu et al. |
| 2011/0060336 | A1 | 3/2011 | Pool et al. |
| 2011/0257655 | A1 | 10/2011 | Copf et al. |
| 2012/0019341 | A1 | 1/2012 | Gabay et al. |
| 2012/0019342 | A1 | 1/2012 | Gabay et al. |
| 2012/0035661 | A1 | 2/2012 | Pool et al. |
| 2012/0053633 | A1 | 3/2012 | Stauch |
| 2012/0088953 | A1 | 4/2012 | King |
| 2012/0109207 | A1 | 5/2012 | Trieu |
| 2012/0179215 | A1 | 7/2012 | Soubeiran |
| 2012/0203282 | A1 | 8/2012 | Sachs et al. |
| 2012/0283781 | A1 | 11/2012 | Arnin |
| 2012/0329882 | A1 | 12/2012 | Messersmith et al. |
| 2013/0253344 | A1 | 9/2013 | Griswold et al. |
| 2013/0296940 | A1 | 11/2013 | Northcutt et al. |
| 2014/0005788 | A1 | 1/2014 | Haaja et al. |
| 2014/0025172 | A1 | 1/2014 | Lucas et al. |
| 2014/0052134 | A1 | 2/2014 | Orisek |
| 2014/0142631 | A1 | 5/2014 | Hunziker |
| 2014/0236311 | A1 | 8/2014 | Vicatos et al. |
| 2014/0296918 | A1 | 10/2014 | Fening et al. |
| 2014/0324047 | A1 | 10/2014 | Zahrly et al. |
| 2015/0105824 | A1 | 4/2015 | Moskowitz et al. |

OTHER PUBLICATIONS

Li, G. et al., Case report: Bone transport over an intramedullary nail: A case report with histologic examination of the regenerated Segment. Injury, Int'l. J. Care Injured 30 (1999) 525-534, Elsevier, Oxford, United Kingdom.

Kucukkaya, M. et al., The New Intramedullary Cable Bone Transport Technique, J. Orthop Trauma, 23:7 (2009) 531-536, Raven Press, New York, U.S.A.

Oh, C. et al., Bone transport over an intramedullary nail for reconstruction of long bone defects in tibia, Arch Orthop Trauma Surg, 128:8 (2008) 801-808. Springer, New York, U.S.A.

* cited by examiner

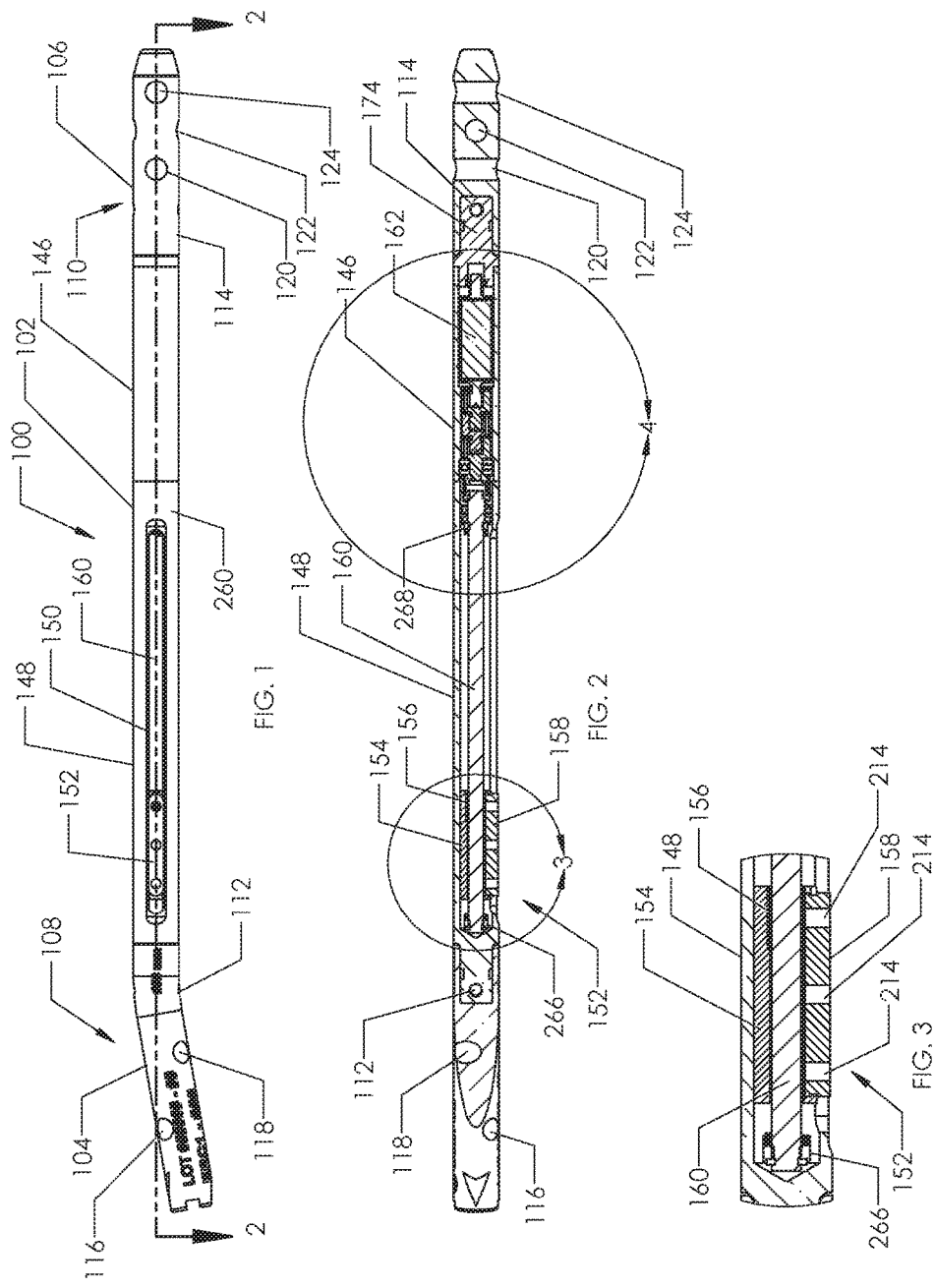

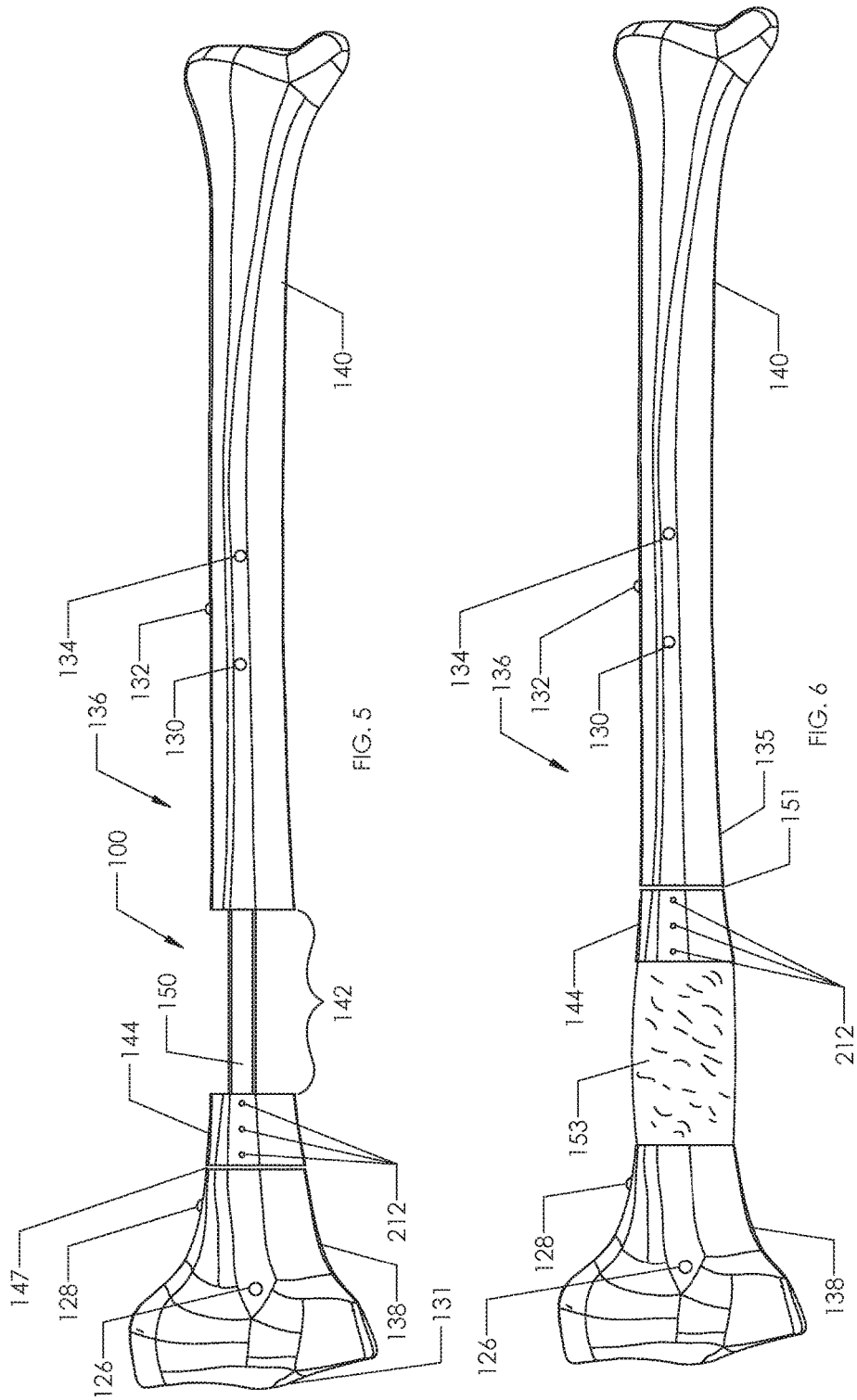

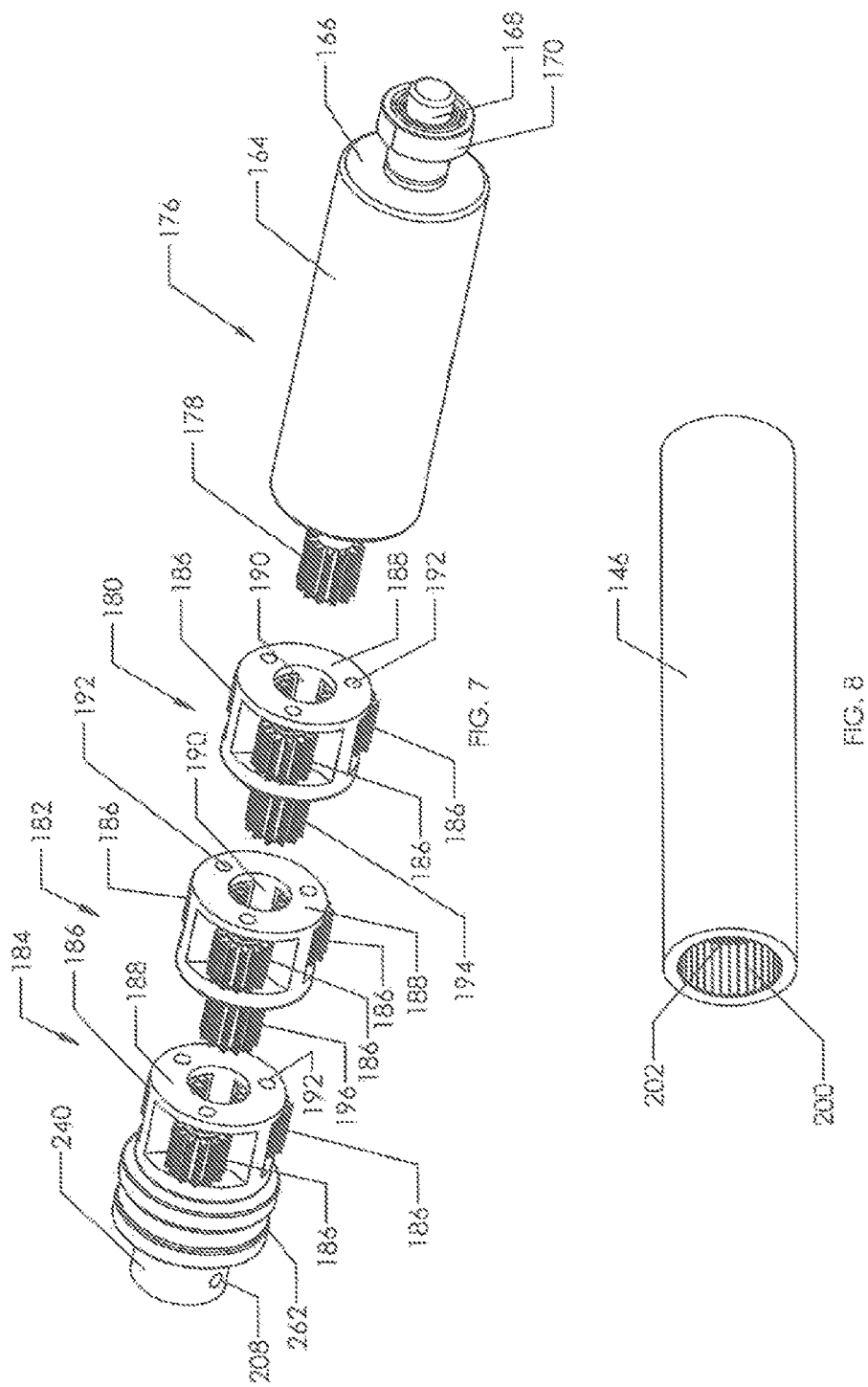

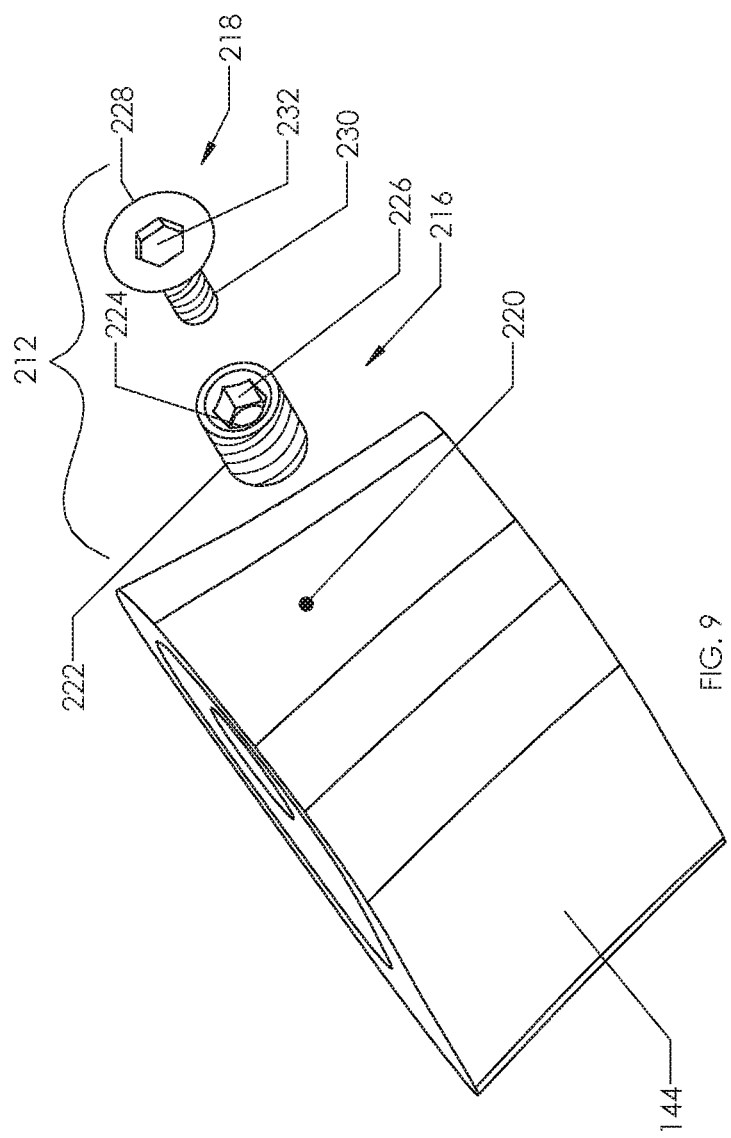

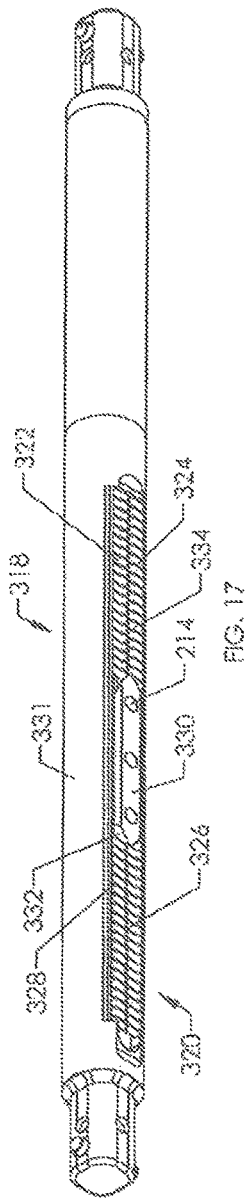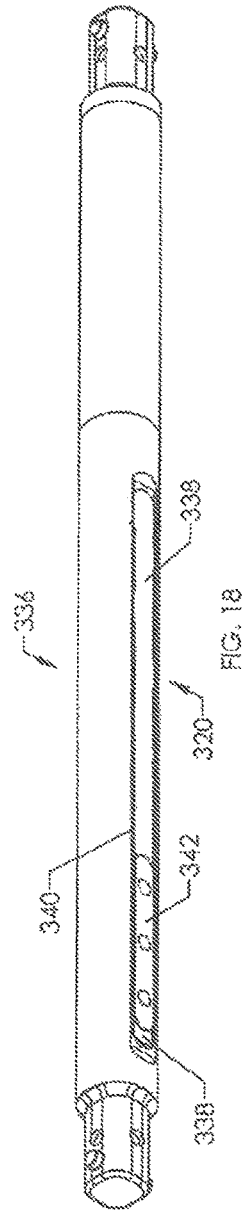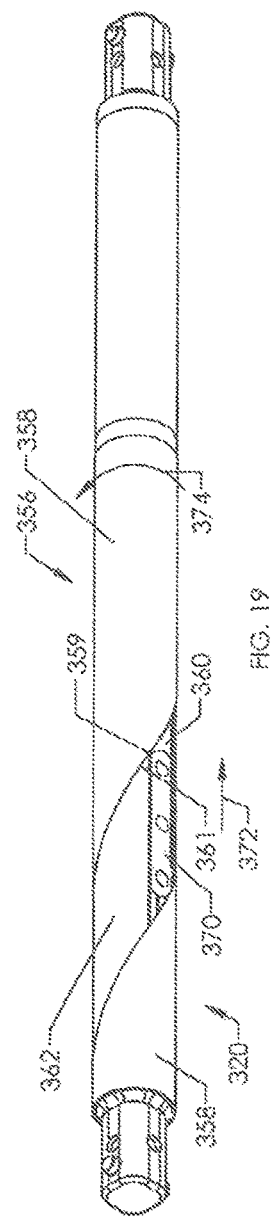

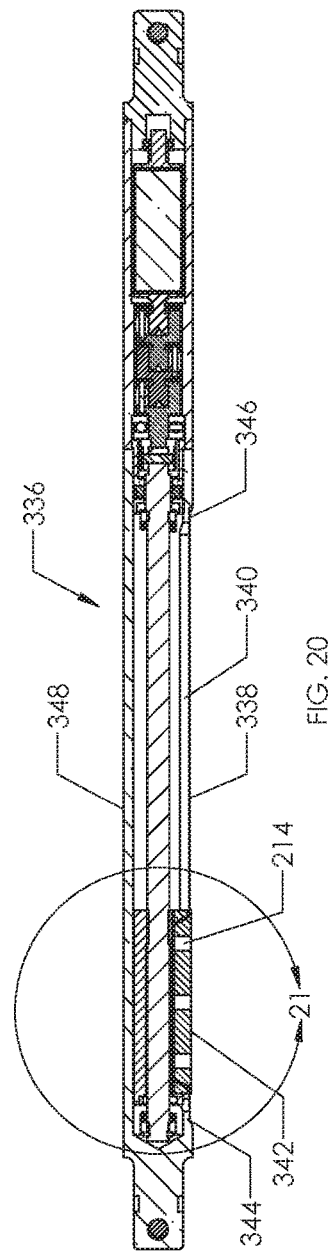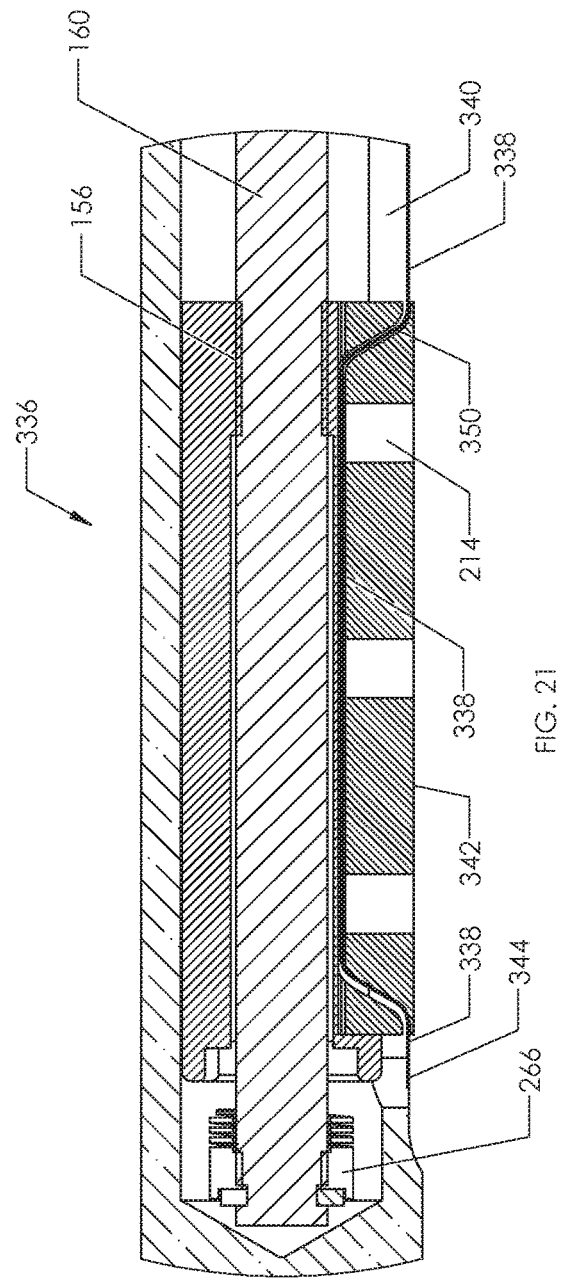

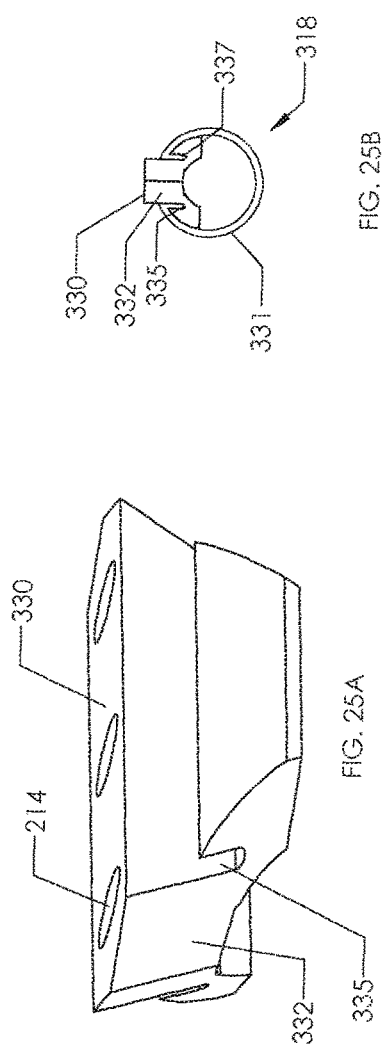
FIG. 25A
FIG. 25B
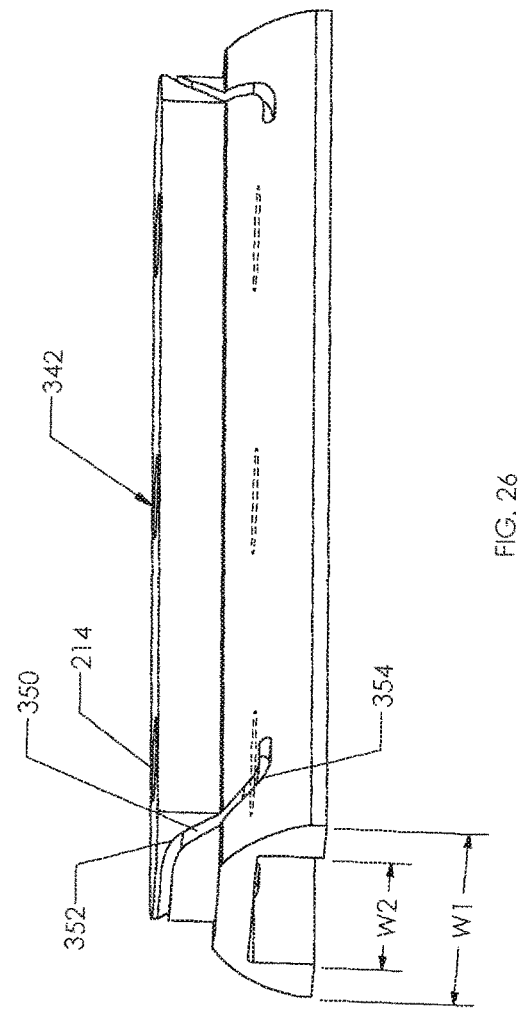
FIG. 26

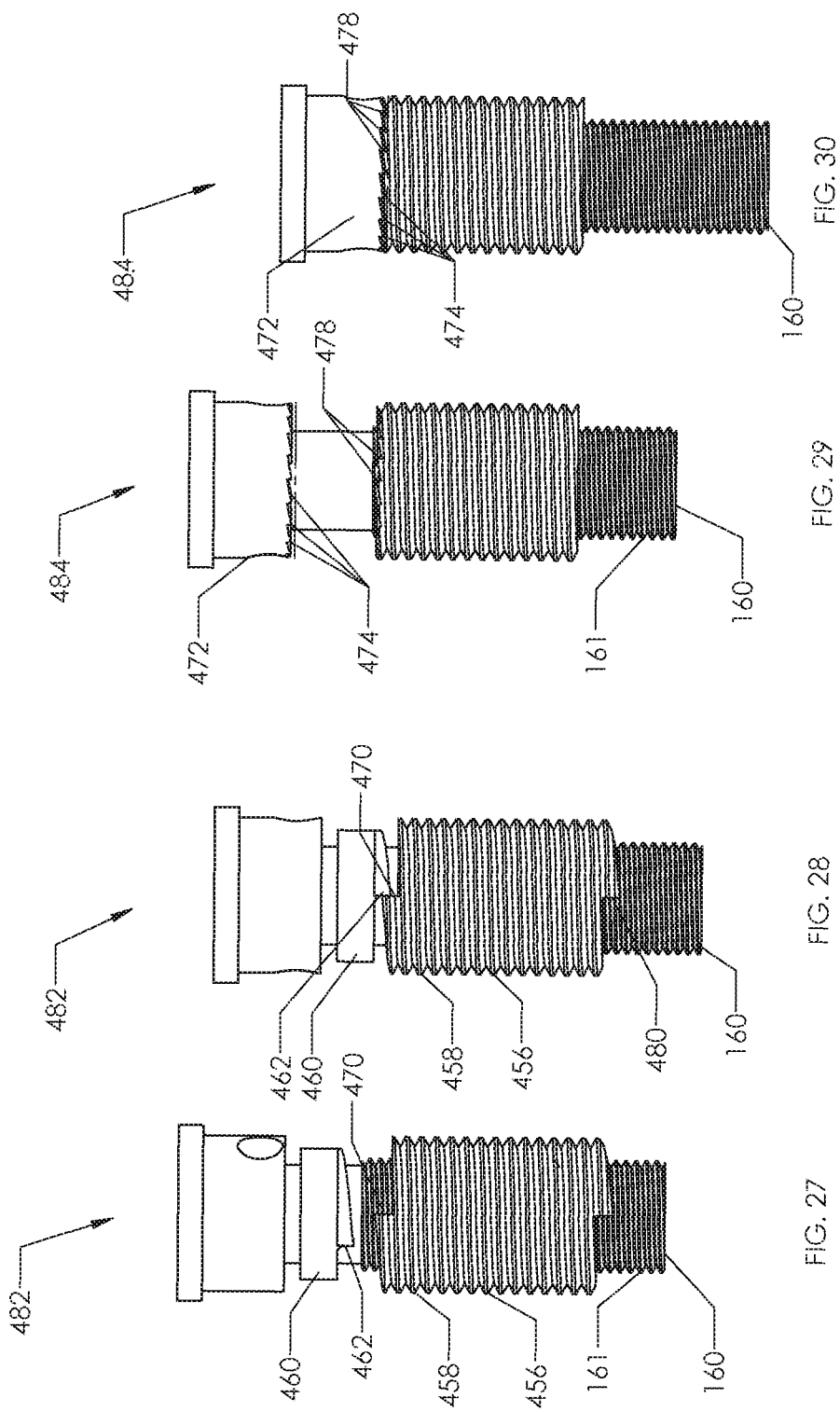

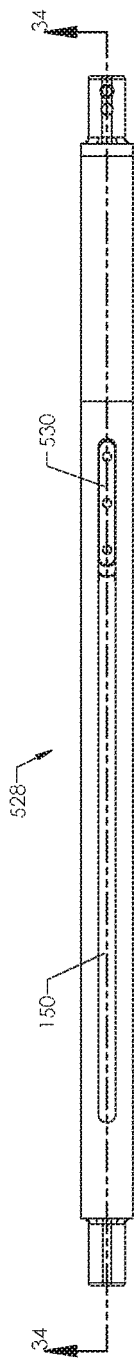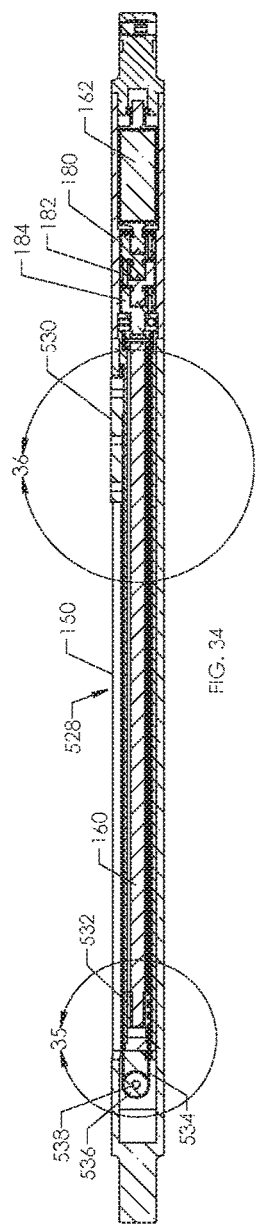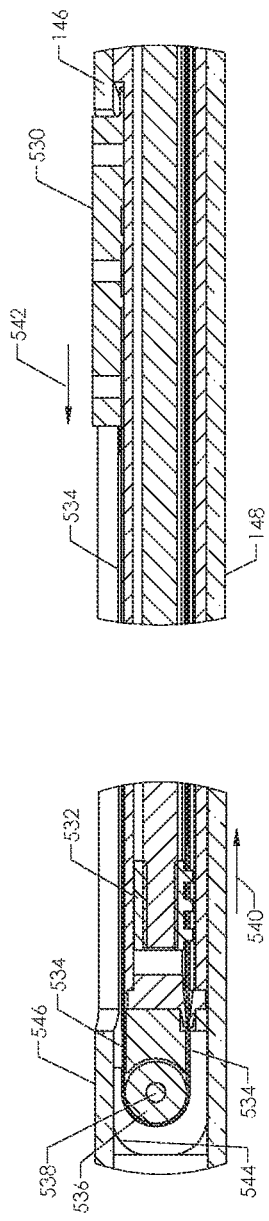

INTRAMEDULLARY IMPLANTS FOR REPLACING LOST BONE

INCORPORATION BY REFERENCE TO ANY PRIORITY APPLICATIONS

This application is a continuation of U.S. patent application Ser. No. 14/451,190, filed Aug. 4, 2014, which is a continuation of U.S. patent application Ser. No. 13/655,246, filed Oct. 18, 2012, now U.S. Pat. No. 9,044,281. Any and all applications for which a foreign or domestic priority claim is identified in the Application Data Sheet as filed with the present application are hereby incorporated by reference under 37 CFR 1.57.

BACKGROUND OF THE INVENTION

Field of the Invention

The field of the invention generally relates to medical devices for treating disorders of the skeletal system.

Description of the Related Art

Distraction osteogenesis is a technique which has been used to grow new bone in patients with a variety of defects. For example, limb lengthening is a technique in which the length of a bone (for example a femur or tibia) may be increased. By creating a corticotomy, or osteotomy, in the bone, which is a cut through the bone, the two resulting sections of bone may be moved apart at a particular rate, such as one (1.0) mm per day, allowing new bone to regenerate between the two sections as they move apart. This technique of limb lengthening is used in cases where one limb is longer than the other, such as in a patient whose prior bone break did not heal correctly, or in a patient whose growth plate was diseased or damaged prior to maturity. In some patients, stature lengthening is desired, and is achieved by lengthening both femurs and/or both tibia to increase the patient's height.

Bone transport is a similar procedure, in that it makes use of osteogenesis, but instead of increasing the distance between the ends of a bone, bone transport fills in missing bone in between. There are several reasons why significant amounts of bone may be missing. For example, a prior non-union of bone, such as that from a fracture, may have become infected, and the infected section may need to be removed. Segmental defects may be present, the defects often occurring from severe trauma when large portions of bone are severely damaged. Other types of bone infections or osteosarcoma may be other reasons for a large piece of bone that must be removed or is missing.

Limb lengthening is often performed using external fixation, wherein an external distraction frame is attached to the two sections of bone by pins which pass through the skin. The pins can be sites for infection and are often painful for the patient, as the pin placement site remains a somewhat open wound "pin tract" throughout the treatment process. The external fixation frames are also bulky, making it difficult for patient to comfortably sit, sleep and move. Intramedullary lengthening devices also exist, such as those described in U.S. Patent Application Publication No. 2011/0060336, which is incorporated by reference herein. Bone transport is typically performed by either external fixation, or by bone grafting.

In external fixation bone transport, a bone segment is cut from one of the two remaining sections of bone and is moved by the external fixation, usually at a rate close to one (1.0) mm per day, until the resulting regenerate bone fills the defect. The wounds created from the pin tracts are an even worse problem than in external fixation limb lengthening, as the pins begin to open the wounds larger as the pins are moved with respect to the skin. In bone grafting, autograft (from the patient) or allograft (from another person) is typically used to create a lattice for new bone growth. Bone grafting can be a more complicated and expensive surgery than the placement of external fixation pins.

SUMMARY OF THE INVENTION

In one embodiment of the invention, a bone transport system includes a nail having a proximal end and a distal end, the proximal end configured for securing to a first portion of bone, the distal end configured for securing to a second portion of bone. The system includes a housing having a wall with a longitudinal opening extending a length along a portion thereof. The system further includes a transport sled having a length that is shorter than the length of the longitudinal opening, the transport sled configured for securing to a third portion of bone, the transport sled further configured to be moveable along the longitudinal opening. The system further includes a magnetic assembly disposed within the nail and configured to be non-invasively actuated by a moving magnetic field, wherein actuation of the magnetic assembly moves the transport sled along the longitudinal opening. The system further includes a ribbon extending on opposing sides of the transport sled and substantially covering the longitudinal opening.

In another embodiment of the invention, a bone transport system includes a nail having a proximal end and a distal end, the proximal end configured for securing to a first portion of bone, the distal end configured for securing to a second portion of bone. The system further includes a housing section having a wall with a longitudinal opening extending along a portion thereof and having a length. The system further includes a transport sled having a length that is shorter than the length of the longitudinal opening, the transport sled configured for securing to a third portion of bone, the transport sled further configured to move along the longitudinal opening. The system further includes a magnetic assembly disposed within the nail and configured to be non-invasively actuated by a moving magnetic field, wherein actuation of the magnetic assembly moves the transport sled along the longitudinal opening. The system further includes a dynamic cover which is configured to cover substantially all of the portion of the longitudinal opening that is not occupied by the transport sled independent of the position of the transport sled along the length of the longitudinal opening.

In another embodiment of the invention, a method for performing a bone transport procedure includes placing a bone transport system within an intramedullary canal of a bone, the bone transport system comprising a nail having a proximal end and a distal end, a housing section having a wall with a longitudinal opening extending along a portion thereof, a transport sled disposed in the longitudinal opening and configured to move along the longitudinal opening in response to actuation of a magnetic assembly disposed within the nail, and a dynamic cover configured to cover substantially all of the longitudinal opening not occupied by the transport sled. The method further includes securing the proximal end of the nail to a first portion of bone, securing the distal end of the nail to a second portion of bone, and securing a third portion of bone to the transport sled. The method further includes applying a moving magnetic field to the magnetic assembly to actuate the magnetic assembly and cause the transport sled to move along the longitudinal opening, wherein the dynamic cover substantially covers all of the longitudinal opening regardless of the location of the transport sled within the longitudinal opening.

In another embodiment of the invention, a bone transport system includes a nail having a proximal end and a distal end, the proximal end configured for securing to a first portion of bone, the distal end configured for securing to a second portion of bone. The system further includes a housing section having a wall with a longitudinal opening extending along a portion thereof and having a length. The system further includes a transport sled having a length that is shorter than the length of the longitudinal opening, the transport sled configured for securing to a third portion of bone, the transport sled disposed within the longitudinal opening and further configured to move along the longitudinal opening. The system further includes a magnetic assembly disposed within the nail and configured to be non-invasively actuated by a moving magnetic field, wherein actuation of the magnetic assembly turns a lead screw, which in turn moves the transport sled along the longitudinal opening, and wherein the lead screw includes a threaded surface having a coating thereon, the coating selected from either molybdenum disulfide or amorphous diamond-like carbon.

In another embodiment of the invention, and implantable dynamic apparatus includes a nail having a first portion and a second portion, the first portion of the nail configured for securing to a first portion of bone, the second portion of the nail configured for securing to a second portion of bone, the second portion of the nail configured to be longitudinally moveable with respect to the first portion of the nail, wherein the second portion of the nail includes an internally threaded feature. The apparatus further includes a magnetic assembly configured to be non-invasively actuated by a moving magnetic field. The apparatus further includes a lead screw having an externally threaded portion, the lead screw coupled to the magnetic assembly, wherein the externally threaded portion of the lead screw engages the internally threaded feature of the second portion of the nail, wherein actuation of the magnetic assembly turns the lead screw, which in turn changes the longitudinal displacement between the first portion of the nail and the second portion of the nail. The apparatus further includes a first abutment surface coupled to the lead screw, a second abutment surface coupled to the second portion of the nail, and wherein the turning of the lead screw in a first direction causes the first abutment to contact the second abutment, stopping the motion of the lead screw with respect to the second portion of the nail, and wherein subsequent turning of the nail in a second direction is not impeded by any jamming between the internally threaded feature and the externally threaded portion.

In another embodiment of the invention, a bone transport system includes a nail having a proximal end and a distal end, the proximal end configured for securing to a first portion of bone, the distal end configured for securing to a second portion of bone. The system further includes a housing section having a wall with a longitudinal opening extending along a portion thereof. The system further includes a transport sled configured for securing to a third portion of bone, the transport sled disposed within the longitudinal opening and further configured to be moveable along the longitudinal opening, the transport sled having a first stopping surface. The system further includes a magnetic assembly disposed within the nail and configured to be non-invasively actuated by a moving magnetic field, wherein actuation of the magnetic assembly rotates a lead screw operatively coupled thereto and moves the transport sled along the longitudinal opening. The system further includes a stop secured to the lead screw and having a second contact surface, and wherein when the first contact surface contacts the second contact surface in response to rotation of the lead screw, the stop is configured to radially expand and prevent additional rotation of the lead screw.

In another embodiment of the invention, a non-invasively adjustable implant includes a nail having a first portion and a second portion, the first portion of the nail configured for securing to a first portion of bone, the second portion of the nail configured for securing to a second portion of bone, the second portion of the nail configured to be longitudinally moveable with respect to the first portion of the nail. The implant further includes a magnetic assembly configured to be non-invasively actuated. The system further includes a cylindrical permanent magnet having at least two radially-directed poles, the cylindrical permanent magnet configured to be turned by a moving magnetic field, the cylindrical permanent magnet held by a magnet holder, the magnet holder rotationally coupled to the magnetic assembly, wherein actuation of the magnetic assembly changes the longitudinal displacement between the first portion of the nail and the second portion of the nail. The implant further includes a friction applicator which couples the magnet holder to the cylindrical permanent magnet, wherein the friction applicator is configured to apply a static frictional torque to the magnet so that when a moving magnetic field couples to the cylindrical permanent magnet at a torque below the static frictional torque, the cylindrical permanent magnet and the magnet hold turn in unison, and when a moving magnetic field couples to the cylindrical permanent magnet at a torque above the static frictional torque, the cylindrical permanent magnet turns while the magnet holder remains rotationally stationary.

In another embodiment of the invention, a bone transport system includes a nail having a proximal end and a distal end, the proximal end configured for securing to a first portion of bone, the distal end configured for securing to a second portion of bone. The system further includes a housing section having a wall with a longitudinal opening extending along a portion thereof. The system further includes a transport sled configured for securing to a third portion of bone, the transport sled disposed within the longitudinal opening and further configured to be moveable along the longitudinal opening. The system further includes a magnetic assembly disposed within the nail and configured to be non-invasively actuated by a moving magnetic field, wherein actuation of the magnetic assembly moves the transport sled along the longitudinal opening, the magnetic assembly having a magnetic housing containing a permanent magnet therein and a biasing member interposed between the magnetic housing and the permanent magnet, wherein the magnetic housing and the permanent magnet are rotationally locked by the biasing member up to a threshold torque value.

In another embodiment of the invention, a bone transport system includes a nail having a proximal end and a distal end, the proximal end configured for securing to a first portion of bone, the distal end configured for securing to a second portion of bone. The system further includes a housing having a wall with a longitudinal opening extending along a portion thereof. The system further includes a transport sled disposed within the longitudinal opening and further configured to be moveable along the longitudinal opening. The system further includes a magnetic assembly disposed within the nail and configured to be non-invasively actuated by a moving magnetic field, wherein actuation of the magnetic assembly rotates a lead screw operatively coupled to a nut moveable along a length of the lead screw in response to rotation thereof. The system further includes a ribbon secured to the nut at one end and secured to the transport sled at an opposing end, the ribbon passing over at least one pulley, wherein movement of the nut in a first direction translates into movement of the transport sled in a second, opposing direction.

In another embodiment of the invention, a method for performing a bone transport procedure includes preparing the medullary canal of a bone for placement of a nail configured to change its configuration at least partially from a moving magnetic field supplied by an external adjustment device, the change in configuration including the longitudinal movement of a transport sled. The method further includes placing a nail within the medullary canal of the bone, securing a first end of the nail to a first portion of the bone, and securing a second end of the nail to a second portion of the bone. The method further includes storing information in the external adjustment device, the information including the orientation of the nail within the bone and the direction of planned movement of the transport sled.

In another embodiment of the invention, a bone transport system includes a nail having a first end and a second end, the first end configured for securing to a first portion of bone, the second end configured for securing to a second portion of bone. The system further includes a magnetic assembly disposed within the nail and configured to be non-invasively actuated by a moving magnetic field, wherein actuation of the magnetic assembly rotates a lead screw operatively coupled to a nut moveable along a length of the lead screw in response to rotation thereof, the nut containing at least one pulley affixed thereto. The system further includes at least one pulley disposed within the nail at the first end. The system further includes at least one tension line fixed relative to the first end and passing over both the at least one pulley of the nut and the at least one pulley disposed within the nail at the first end, and wherein the tension line is configured to be secured to a third portion of bone.

In another embodiment of the invention, a bone transport system includes a nail having a proximal end and a distal end, the proximal end configured for securing to a first portion of bone, the distal end configured for securing to a second portion of bone. The system further includes a housing section having a wall with a longitudinal opening extending along a portion thereof. The system further includes a transport sled configured for securing to a third portion of bone, the transport sled disposed within the longitudinal opening and further configured to be moveable along the longitudinal opening. The system further includes a magnetic assembly disposed within the nail and configured to be non-invasively actuated by a moving magnetic field, wherein actuation of the magnetic assembly moves the transport sled along the longitudinal opening, and wherein the nail has an ultimate failure torque greater than 19 Newton-meters.

BRIEF DESCRIPTION OF THE DRAWINGS

FIG. 1 illustrates an intramedullary bone transport device for replacing lost bone according to one embodiment.
FIG. 2 illustrates a longitudinal section of the intramedullary bone transport device of FIG. 1.
FIG. 3 illustrates detail 3 of FIG. 2.
FIG. 5 illustrates the intramedullary bone transport device secured within the medullary canal of a tibia, prior to transporting a bone segment.
FIG. 6 illustrates the intramedullary bone transport device secured within the medullary canal of a tibia, after transporting a bone segment.
FIG. 7 illustrates an exploded view of the internal components located within an enclosed housing portion of an actuator of the intramedullary bone transport device.
FIG. 8 illustrates an enclosed housing portion of the actuator of the intramedullary bone transport device.
FIG. 9 illustrates a screw assembly for securing a transport sled to a bone segment.
FIG. 17 illustrates the actuator of an intramedullary bone transport device having a dynamic cover according to a first embodiment.
FIG. 18 illustrates the actuator of an intramedullary bone transport device having a dynamic cover according to a second embodiment.
FIG. 19 illustrates the actuator of an intramedullary bone transport device having a dynamic cover according to a third embodiment.
FIG. 20 is a longitudinal section of the actuator of FIG. 18.
FIG. 21 illustrates detail 21 of the actuator of FIG. 20.
FIG. 25A illustrates the transport sled of the intramedullary bone transport device of FIG. 17.
FIG. 25B illustrates a cross-section of the transport sled in the open housing of the intramedullary bone transport device of FIG. 17.
FIG. 26 illustrates the transport sled of the intramedullary bone transport device of FIG. 18.
FIG. 27 illustrates an alternative embodiment of an end stop prior to reaching the end of travel.
FIG. 28 illustrates the end stop of FIG. 27 at the end of travel in one direction.
FIG. 29 illustrates an additional embodiment of an end stop prior to reaching the end of travel.
FIG. 30 illustrates the end stop of FIG. 29 at the end of travel in one direction.

FIG. 33 illustrates an intramedullary bone transport device having an alternative drive system.

FIG. 34 illustrates a longitudinal section of the intramedullary bone transport device of FIG. 33 taken along lines 34-34.

FIG. 35 illustrates detail 35 of FIG. 34.

FIG. 36 illustrates detail 36 of FIG. 34.

DETAILED DESCRIPTION OF THE PREFERRED EMBODIMENT

Figure 4:
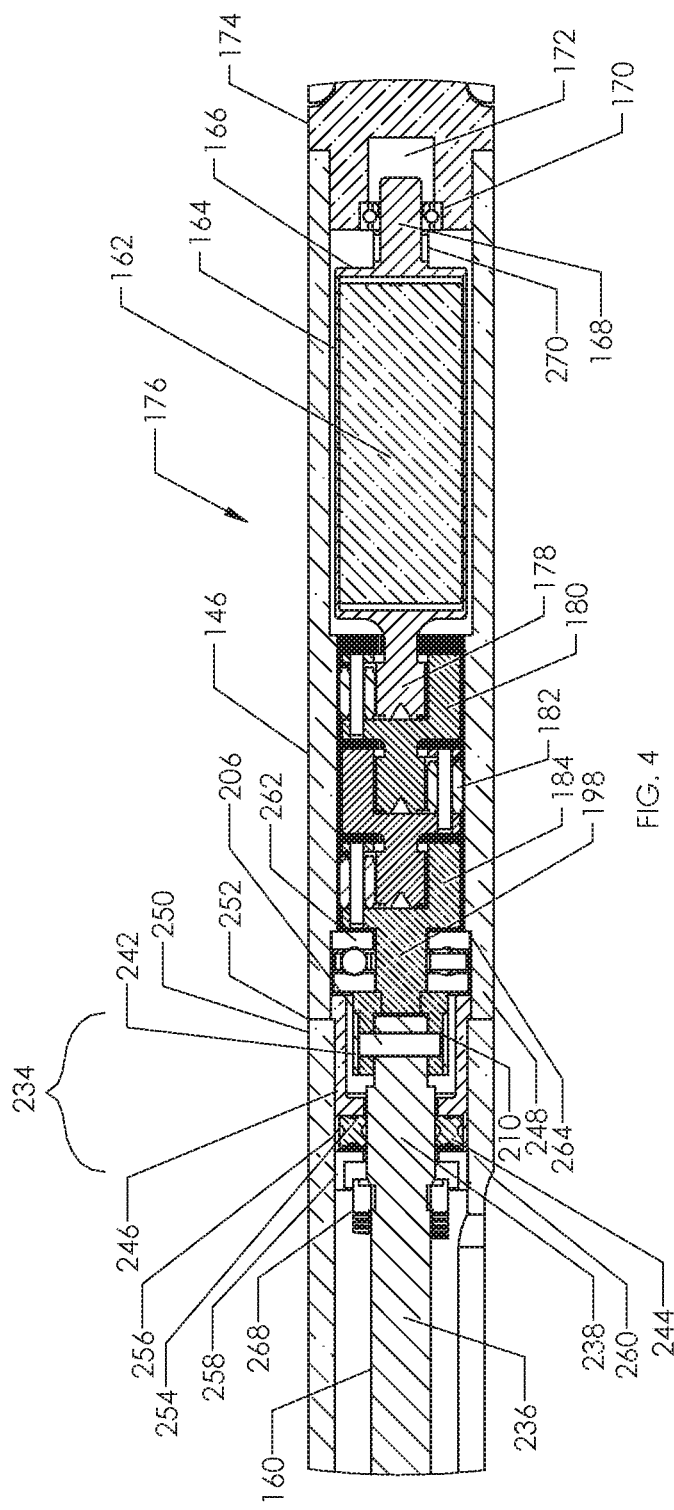
FIG. 4 illustrates detail 4 of FIG. 2.

FIG. 1 illustrates an intramedullary bone transport device 100 in a "nail" configuration, having an actuator 102, a first extension rod 104 coupled to the actuator 102 at a first end 108 of the intramedullary bone transport device 100, and a second extension rod 106 coupled to the actuator 102 a second end 110 of the intramedullary bone transport device 100. First extension rod 104 and second extension rod 106 are secured to actuator 102 by set screws 112, 114. A variety of different extension rods are available, each having a particular angulation and length. In FIG. 1, first extension rod 104 is angled for use in the proximal tibia while second extension rod 106 is straight for use in the distal tibia. Multiple configurations are contemplated for tibial use, as well as antegrade use in the femur and retrograde use in the femur. Holes 116, 118, 120, 122, 124 are configured with specific diameters and orientations, in order to accommodate bone screws 126, 128, 130, 132, 134 for securing intramedullary bone transport device 100 to the bone as seen in FIGS. 5 and 6. FIGS. 5 and 6 show the intramedullary bone transport device 100 secured in the medullary canal of a tibia 136. The tibia 136 is shown having a proximal portion 138 and a distal portion 140. Additionally, there is a missing section 142 of tibia 136. The bone that was originally in this missing section 142 may be missing because of several reasons. It may have been destroyed because of severe trauma to this area of the tibia. It may also have been removed as part of a treatment of osteosarcoma in this area. The intramedullary bone transport device 100 facilitates the replacement of this bone by facilitating the controlled movement of a bone segment 144, which can be cut from one of the two portions 138, 140 of the tibia 136. In the case illustrated in FIGS. 5 and 6, the bone segment 144 is cut from the proximal portion 138 of the tibia 136.

Returning to FIG. 1, the actuator 102 includes an enclosed housing 146 and an open housing 148. The open housing 148 contains a longitudinal slit 150 on one side along which a transport sled 152 is configured for axial movement. Longitudinal slit has a length of 140 mm, but can be a range of lengths, depending on the desired amount of bone transport. Referring more specifically to FIGS. 2, 3 and 4, the transport sled 152 includes a moveable transport tube 154 having an internal nut 156. A support stage 158 is attached to the transport tube 154, the support stage 158 being configured for axial movement within the longitudinal slit 150 of the open housing 148. The internal nut 156 is threaded and coupled to a correspondingly threaded lead screw 160, so that rotation of the lead screw 160 in a first rotational direction causes the transport tube 154 and support stage 158 (i.e., transport sled 152) to move along the longitudinal slit 150 in a first axial direction and rotation of the lead screw 160 in a second, opposite rotational direction causes the transport sled 152 to move along the longitudinal slit 150 in a second axial direction, opposite of the first axial direction. Internal nut 156 may have female threads cut directly into the transport tube 154. Alternatively, internal nut 156 may have external male threads and the transport tube 154 may have internal female threads, so that the internal female threads of the transport tube 154 and the external male threads of the internal nut 156 create a helical engagement surface. The two parts may be held together at this surface with adhesive, epoxy, etc. A representative thread design is 80 turns per inch.

Intramedullary bone transport device 100 is configured to allow controlled, precise translation of the transport sled 152 along the length of the longitudinal slit 150 by non-invasive remote control, and thus controlled, precise translation of the bone segment 144 that is secured to the transport sled 152. Within the enclosed housing 146 of the actuator 102 is located a rotatable magnetic assembly 176. Further detail can be seen in FIGS. 7 and 8. The magnetic assembly 176 includes a cylindrical, radially-poled permanent magnet 162 (FIG. 22) contained within a magnet housing 164 having an end cap 166. The permanent magnet 162 may include rare earth magnet materials, such as Neodymium-Iron-Boron. The permanent magnet 162 has a protective Phenolic coating and may be held statically within the magnet housing 164 and end cap 166 by epoxy or other adhesive. The magnet housing 164, end cap 166 and epoxy form a seal to further protect the permanent magnet 162. Magnet housing 164 may also be welded to end cap 166 to create a hermetic seal. End cap 166 includes cylindrical extension or axle 168 which fits within the inner diameter of a radial bearing 170, allowing for low friction rotation. Outer diameter of radial bearing 170 fits within cavity 172 of an actuator end cap 174 as seen, for example, in FIG. 4. Actuator end cap 174 may be welded to enclosed housing 146 of actuator 102. Referring to FIG. 7, the magnetic assembly 176 terminates at an opposing end in a first sun gear 178 which is integral to magnet housing 164. First sun gear 178 may also be made as a separate component and secured to magnet housing 164, for example by welding. First sun gear 178 turns with rotation of magnetic assembly 176 (in a 1:1 fashion) upon application of a moving magnetic field applied to the patient from an external location. The first sun gear 178 is configured to insert within opening 190 of a first gear stage 180 having three planetary gears 186 which are rotatably held in a frame 188 by axles 192. Second sun gear 194, which is the output of the first gear stage 180, turns with frame. The identical components exist in second gear stage 182, which outputs to a third sun gear 196, and third gear stage 184, which outputs to an output shaft 198 as best seen in FIG. 4. Along the length that the gear stages 180, 182, 184 extend, the inner wall 200 of enclosed housing 146 (as seen in FIG. 8) has internal teeth 202 along which the externally extending teeth 204 of the planetary gears 186 engage, as they turn. Each gear stage illustrated has a 4:1 gear ratio, so the output shaft 198 turns once for every 64 turns of the magnetic assembly 176. The output shaft 198 is coupled to lead screw 160 by a pin 206 (FIG. 4) which passes through holes 208 in a lead screw coupling cup 240 (FIG. 7) which is welded to output shaft 198 and a hole 210 in the lead screw 160 (FIG. 4). Pin 206 is held in place by retaining cylinder 242. A pin 206 diameter of 0.055 inches on a pin 206 made from 400 series stainless steel allows for a tensile break force of over 600 pounds between the lead screw 160 and the lead screw coupling cup 240. The torque applied on the magnetic assembly 176 by the action of the rotating magnetic field on the cylindrical permanent magnet 162, is therefore augmented on the order of 64 times in terms of the turning torque of the lead screw 160. This allows the transport sled 152 to be able to move with high precision. Returning to FIGS. 5 and 6, bone segment 144 is attached to transport sled 152 by three screw assemblies 212, which engage with internally threaded holes 214 of the support stage 158 of the transport sled 152. Because of the 64:1 gear ratio, the intramedullary bone transport device is able to axially displace the bone segment 144 against severe resisting forces, for example those created by soft tissue. A thrust bearing 262 (FIG. 4) is sandwiched between the lead screw 160 and the gear stages 180, 182, 184 in order to protect the gear stages 180, 182, 184 and the magnetic assembly 176 from high compressive forces. The thrust bearing 262 butts up against a flange 264 inside the enclosed housing 146. A shim spacer 270 can be added to assembly in order to maintain a desired amount of axial play. Shim spacer 270 can be a tube, chosen from a variety of lengths to optimize this axial spacing of the components.

FIG. 9 illustrates a bone segment 144 and a screw assembly 212 for securing the bone segment 144 to the support stage 158 of the transport sled 152. For clarity purposes, the remainder of the tibia is not shown, nor is the transport sled, which would be located inside the reamed medullary canal of the bone segment 144. A drill site 220 is chosen for drilling through the bone segment 144. This drill site 220 corresponds to one of the threaded holes 214 of the support stage 158 of the transport sled 152, and is located using fluoroscopy or surgical navigation during the surgical procedure. The holes 214 themselves may be made with radiopaque markings to further locate them. The cortex of a single wall of the bone segment 144 is drilled at the drill location 220 to make a pilot hole. A conventional tap (not shown) may then be used to cut internal threads in the bone at the drill location. Cannulated screw 216 is then secured into the tapped hole with external threads 222 engaging with tapped threads. Alternatively, if the cannulated screw 216 is self-tapping, then the initial hole need only be piloted. Cannulated screw is tightened into place with a hex driver, which engages with female hex 226. Torx® shapes may be used instead of hex shapes. Inner screw 218, having a head 228 and a threaded shaft 230 is then placed through a non-threaded through hole 224 in the cannulated screw 216 and threaded shaft 230 is engaged with and tightened into threaded hole 214 of the support stage 158 of the transport sled 152. Hex driver is placed into female hex 232 to tighten inner screw 218. As illustrated in FIGS. 5 and 6, there may be three of these connections made, to connect three screw assemblies 212 with the three threaded screw holes 214 of the support stage 158 of the transport sled 152, though at times it might be desired to make fewer than three connections or even more than three connections.

Referring back to FIG. 4, the gear stages 180, 182, 184 and the magnetic assembly 176 are protected from any biological material that may enter longitudinal slit 150, by a dynamic seal assembly 234. The lead screw 160 includes a long threaded portion 236 and a smooth diameter (non-threaded) portion 238. An O-ring 244 having an "X" cross-section seals over the outer diameter of the smooth diameter portion 238 and maintains the seal during rotation. A retaining structure 246 is welded with termination 248 of enclosed housing 146 and termination 250 of open housing at weld point 252. A face 254 of retaining structure 246 serves as an axial abutment of O-ring 244 while longitudinal extension 256 of retaining structure 246 retains O-ring 244 at its outer diameter. The retaining structure 246 also further retains thrust bearing 262. A seal gland 258 presses or snaps in place within the inner diameter of enclosed portion 260 of open housing, to further retain O-ring 244. The O-ring 244 material may be EPDM or other similarly performing material.

The majority of components in the intramedullary bone transport device can be made of titanium, or titanium alloys, or other metals such as stainless steel or cobalt chromium. Bearings 170, 262 and pin 206 can be made of 400 series stainless steel. A 10.7 mm diameter actuator having a longitudinal slit 150 length of approximately 134 mm has a total transport length of 110 mm. A 10.7 mm diameter actuator having a longitudinal slit 150 length of approximately 89 mm allows for a total transport length of 65 mm. A torsional finite element analysis was performed on a Titanium-6-4 alloy actuator having these dimensions. The yield torque was 25 Newton-meters. This compares favorably to commonly used trauma nails, some of which experience failure (ultimate torque) at 19 Newton-meters. Yield torque is defined as the torque at which the nail begins to deform plastically, and thus the ultimate torque of the 10.7 mm diameter actuator is above the 25 Newton-meter yield torque.

Figure 10:
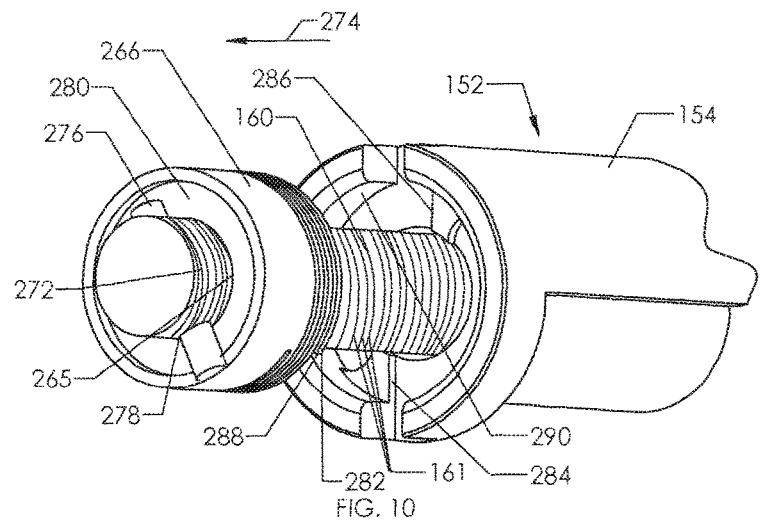
FIG. 10 illustrates detail view of an end stop for avoiding jamming of a transport sled.

In FIGS. 2 through 4, the transport sled 152 abuts end stops 266, 268 at each respective end of its travel over the lead screw 160. FIG. 10 illustrates an end stop 266 having a threaded inner diameter 265 configured for engaging the external threads 161 of lead screw 160. Pin 276 is fit through hole 278 on end 272 of lead screw 160, and is sized so that pin 276 fits within the inner diameter of counterbore 280 on end stop 266, thus limiting the axial travel of the end stop 266 in first axial direction 274. An analogous assembly may be used, using instead a c-clip which clips over a circumferential groove around the end 272 of the lead screw 160, thus replacing the hole 278 and the pin 276. Still referring to FIG. 10, a spring portion 282 is laser cut at one end of end stop 266. End of transport tube 154 includes ledges 284, 286 which are configured so that when transport tube 154 approaches end stop 266, the end 288 of spring portion 282 abuts one of the ledges 284, 286. Because the end stop 266 is held statically by combination of counterbore 280, threads 161, 265, and pin 276, the end 288 places a tangential force on ledge 284 or 286 of transport tube 154. This causes spring portion 282 to increase in diameter until it is restrained by inner wall 290 of transport tube 154. The transport sled 152 is thus stopped axially, and even if a large torque is placed on permanent magnet 162 by an external rotating magnetic field. Thus, even a large force that pushes transport sled 152 will not cause the transport tube 154 to jam with lead screw 160, because the binding is between spring portion 282 of end stop 266 and inner wall 290 of transport tube 154, and not between internal nut 156 and lead screw 160. When subsequently a torque is placed in an opposite direction on permanent magnet 162 by a rotating magnetic field to move the transport sled 152 in a direction opposite the first axial direction 274 the tangential force between the end 288 and one of ledge 286 or 286 decreases, the spring portion 282 decreases in diameter and the transport tube 154 is free to move away from the end 288 of spring portion 282. End stop 268, seen at other end of lead screw 260 in FIG. 4, does not need a pin 276 or c-clip to hold it axially, but instead abuts the increase in diameter between the smaller diameter threaded portion 236 of the lead screw 260 and the smooth diameter portion 238 of the lead screw 260. The spring portion 282 of end stop 266, 268 may alternatively be made from a split lock washer, for simplicity and cost purposes.

Figure 11:
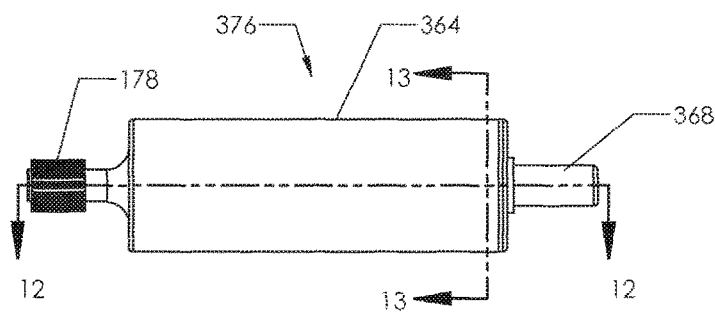
FIG. 11 illustrates a spring friction slip clutch incorporated into a magnetic assembly.
Figures 12, 13:
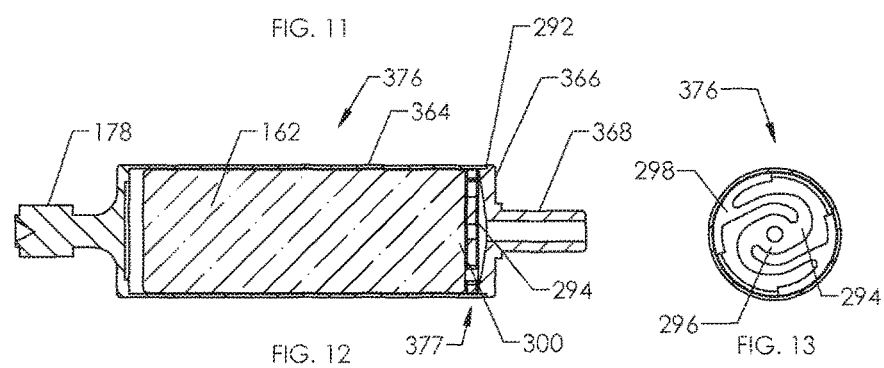
FIG. 12 illustrates a longitudinal section of FIG. 11, taken along lines 12-12.
FIG. 13 illustrated a cross-section of FIG. 11, taken along lines 13-13.

FIGS. 11-13 illustrate an alternative magnetic assembly 376 having a spring friction slip clutch 377. The slip clutch 377 serves to limit the maximum amount of force applied on the body tissue, in this case the bone segment 144 and its neighboring soft tissue. It should be noted that the assembly described may be used on other devices that are not bone transport devices, for example, limb lengthening devices, spine distraction devices, jaw distraction devices and cranial distraction devices in which too large of a torque applied to the permanent magnet 162 results in too large of a distraction force, and thus possible damage to tissue or pain. In the alternative magnetic assembly 376, the permanent magnet 162 is held inside a magnetic housing 364 and an end cap 366 having a cylindrical extension or axle 368. In this case, however, the permanent magnet 162 is not bonded in place, but is held in place with respect to the magnetic housing 364 and end cap 366 by the use of friction. The magnetic housing 364 and end cap 366 are welded together along a circumferential weld 292. A spring 294 is laser cut or etched from a material such as superelastic Nitinol®, and may be heat formed so that center portion 296 is axially displaced from outer portion 298, giving it spring capabilities in the axial direction. FIG. 12 shows the spring 294 trapped between the permanent magnet 162 and the end cap 366, so that the center portion 296 of spring 294 is axially compressed and therefore places a normal force on the end 300 of the permanent magnet 162. By controlling the material, the thickness and the dimensions of the spring 294, a controlled spring constant is achieved, thus applying a consistent normal force, and proportional frictional torque that must be overcome in order to allow permanent magnet 162 to rotate freely within magnet housing 364 and end cap 366. For example, in a scoliosis distraction device, it is desired that at a torque up to two inch-pounds (0.23 Newton-meter), the permanent magnet 162 and the magnet housing/end cap 364/366 remain static to each other, thus allowing the magnetic assembly 376 to turn the lead screw 160. In this application, the gear stages 180, 182, 184 may be omitted. This represents a distraction force of approximately 125 pounds (556 Newton), at which damage may occur to vertebrae at their attachment point to the implant. Above two inch-pounds, it may be desired that the spring 294 allow the permanent magnet 162 to turn freely with respect to the magnet housing/end cap 364/366, thus stopping the turning of the lead screw. Alternatively, in a bone transport or limb lengthening device having gear stages 180, 182, 184, and a total gear ratio of 64:1, it may be desired that this slippage occur at 0.046 inch-pounds (0.005 Newton-meter). This limit would potentially be desired in order to protect the device itself or to protect the bone or soft tissue, for example in a patient with an intramedullary tibial implant, in which the external moving magnetic field is placed extremely close to the permanent magnet 162, and thus able to apply a significantly large torque to it.

Figure 14:
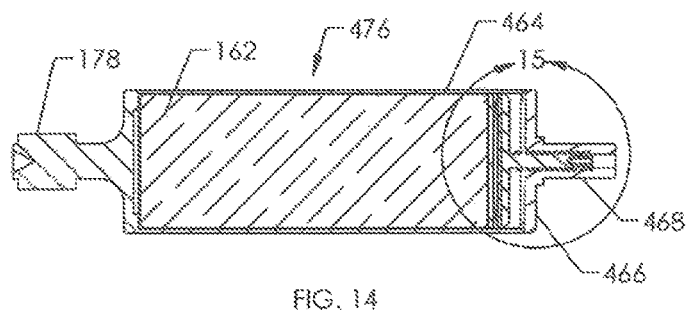
FIG. 14 illustrates an adjustable friction slip clutch incorporated into a magnetic assembly.
Figure 15:
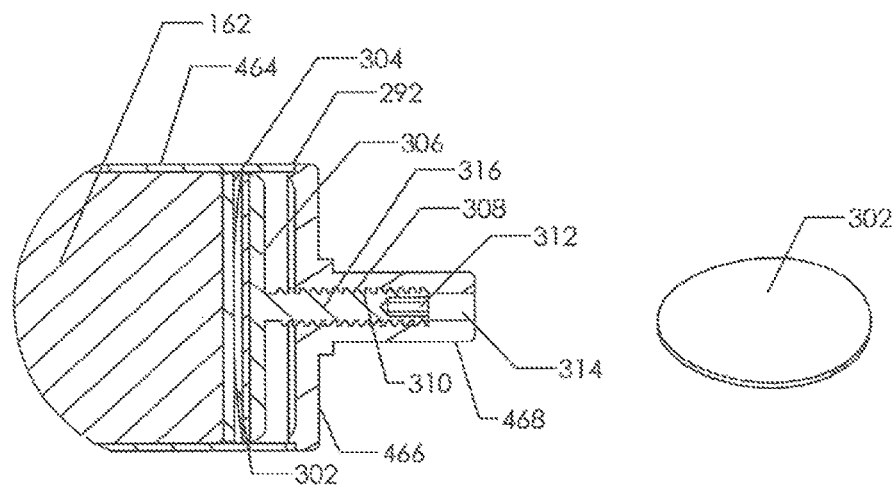
FIG. 15 illustrates detail 15 of FIG. 14.
Figure 16:
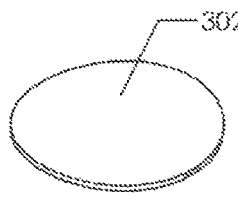
FIG. 16 illustrates a wave disc used as a spring component in the slip clutch of FIGS. 14 and 15.

FIGS. 14-16 illustrate an alternative magnetic assembly 476 which can be adjusted upon assembly in order to set a specific amount of slip torque between the permanent magnet 162 and the magnet housing 464 and end cap 466. A wave disc 302 (similar to a wave washer, but without a center hole) is held between a flat washer 304 and an adjustable compression stage 306. The flat washer 304 serves to protect the permanent magnet 162 and also provide a consistent material surface for friction purposes. The wave disc 302 may be made from stainless steel, and the flat washer 304 may be made from a titanium alloy. Adjustable compression stage 306 has a shaft 316 with a male thread 308 which is engaged within female threads 310 of a cylindrical extension 468. A hex tool may be placed within access hole 314 of the cylindrical extension 468 and into female hex 312 of the shaft 316 of the adjustable compression stage 306. Turning in one direction increases compression on the wave disc 302 and thus increases the normal force and frictional slip torque. Turning in the opposite direction decreases these values. Upon assembly, adhesive may be placed on the threads 308, 310 to permanently bond the adjustable compression stage 306 to the cylindrical extension 468 and maintain the desired amount of frictional slip torque.

The intramedullary bone transport device 100 having a longitudinal slit 150 as shown in FIGS. 1-4 is configured to be implanted within a reamed medullary canal. For example a 10.7 mm diameter device may necessitate reaming to a diameter of 11.0 mm to 13.0 mm. At the beginning of implantation, a certain portion of the longitudinal slit 150 is located where there is no bone (FIG. 5). Because the longitudinal slit 150 is thus exposed to both the internal environment of the medullary canal and the soft tissue (muscle, etc.) of the limb being treated, there is a potential for biological tissue growth on the moveable portions of the mechanism, such as the lead screw 160. One way to protect the threads of the lead screw 160, is by adding a special coating to the surface of the lead screw 160. Coatings may be applied a variety of ways, for example through deposition, and preferably are biocompatible, hard, thin and resistant to adherence of body tissues or fluids. Exemplary coatings include MoST® (based on molybdenum disulfide) or ADLC (Amorphous Diamond-like Carbon).

Though the coating of the lead screw 160 may prevent biological adherence, it may also be desired to prevent any ingrowth or protuberance of bone material into the longitudinal slit 150. One reason that this protuberance may interfere with the treatment of the patient is that it may push against some of the dynamic structures of the bone transport device 100, limiting their functionality. Another reason is that ingrowth of bone into the longitudinal slit 150 may make removal of the bone transport device 100 more difficult, more or less "locking" it in place. Several embodiments of bone transport device 100 having dynamic covers 320 are presented in FIGS. 17 through 19, each dynamic cover 320 with the capability of protecting the longitudinal slit 150 from the ingrowth of bone, while still allowing for the functionality of the transport sled 152 mechanism of the bone transport device 100. FIG. 17 illustrates a bone transport device 318 having a dynamic cover 320 including two opposing combs 322, 324, each of whose teeth extend towards the center line 326 of the longitudinal slit 328. The dynamic cover 320 substantially covers the portion of the longitudinal slit 328 not occupied by the transport sled 152. Comb material may be chosen from superelastic Nitinol, MP35N, Elgiloy® which are biocompatible and have a good combination of strength and repetitive bending characteristics. Individual comb teeth 334 may be 0.105" in length, 0.050" in width and 0.003" in thickness. Transport sled 330 has a specially angled prow 332 on each end, the prows causing the teeth 334 of the combs 322, 324 on each side to be pushed against the side of the slit 328 with relatively low force as the transport sled 330 passes by that particular area. The prow 322 is symmetric along the centerline 326. After the transport sled 330 passes by, the teeth 334 return to their original position covering their half of the slit 328. The angulation of the prow 332, allows the transport sled 330 to slide past the flexing teeth 334 with minimal interference or frictional force. An exemplary included angle of the top of the prow 332 (in relation to the centerline 326) is 60°. A more detailed view of the transport sled 330 is seen in FIGS. 25A and 25B. Grooves 335 on each side of transport sled 330 allow transport sled 330 to ride along rails 337 at edges of slit 328 along the open housing 331 of bone transport device 318.

FIG. 18 illustrates a bone transport device 336 having a dynamic cover 320 having a static ribbon 338 which covers the slit 340. Transport sled 342 is configured to slide over the static ribbon 338. The bone transport device 336 having a static ribbon 338 is shown in more detail in FIGS. 20 and 21. Static ribbon 338 is secured to the open housing 348 at first end 344 and second end 346, both ends adjacent to slit 340. Static ribbon 338 is made of 0.002" thick Nitinol and has a width of 0.140". A detailed view of the transport sled 342 is shown in FIG. 26. The transport sled 342 has a total width (W1) of 0.288". A channel 350 is wirecut in each end of transport sled 342, the channel 350 allows the static ribbon 338 to pass from the outside to the inside of transport sled 342 (and vice versa). During operation, the static ribbon 338 stays in place, while the transport sled 342 slides over it. The channel 350 width (W2) is 0.191", and channel thickness is 0.012" giving enough space for the 0.002" thick static ribbon 338 to slide freely with respect to the transport sled 342. A first radius 352 and a second radius 354 further aid in smooth sliding of the transport sled 342 over the static ribbon 338. The centerline of channel 350 through each radius 352, 354 follows a 0.036" radius. As with many components of the bone transport device 336, the transport sled 342 may be made from Titanium alloy, for example titanium-6Al-4V. Alternatively, the components may be made of cobalt chromium or stainless steel. By controlling the tension at which the static ribbon 338 is held, the dynamic frictional force as the transport sled 342 slides over the static ribbon 338 can be varied, but is typically on the order of about one pound. An alternative to bone transport device 336 is envisioned, wherein the static ribbon 338 is replaced by a ribbon which is fixedly secured to the transport sled 342, and which slides in a similar manner to a conveyor belt.

FIG. 19 illustrates a bone transport device 356 with a dynamic cover 320 having a freely rotatable spiral-cut tube 358 configured to cover the slit 360. Spiral-cut tube 358 has a single spiral gap or cut 362 in its wall, helically oriented along its length. The width of the spiral gap 362 in the axial direction is about the same as the length of the transport sled 370. As the transport sled 370 moves in an axial direction 372, the spiral cut tube 358 is forced to turn in a rotational direction 374, as the leading end 359 transport sled 370 contacts the edge 361 of the spiral cut tube 358 along the spiral gap 362. In this manner, the spiral-cut tube 358 always covers the portion of the slit 360 that is not already covered by the transport sled 370. Spiral-cut tube 358 may be formed from a number of different materials, such as PEEK (polyether ether ketone) or titanium, stainless steel or cobalt chromium.

An alternative to the mechanical dynamic covers 320 of FIGS. 17-19, a self-healing hydrogel may be coated or sprayed over the longitudinal slit 150. Hydrogels of this type have been described in "Rapid self-healing hydrogels" by Phadke et. al., Proceedings of the National Academy of Sciences, Volume 109, No. 12, pages 4383-4388, which is incorporated by reference herein. A self-healing hydrogel acts like molecular Velcro®, and can cover the area of the longitudinal slit 150. As the transport sled 152 moves longitudinally, the hydrogel is slit open in the direction of longitudinal movement of the transport sled 152, while the transport sled 152 moves away from an already slit portion of the hydrogel. By controlling the pH and side chain molecule lengths in the manufacture of the hydrogel, a hydrogel can be made that both allows the slitting by the transport sled 152 and allows the rebinding of the prior slit.

Figure 22:
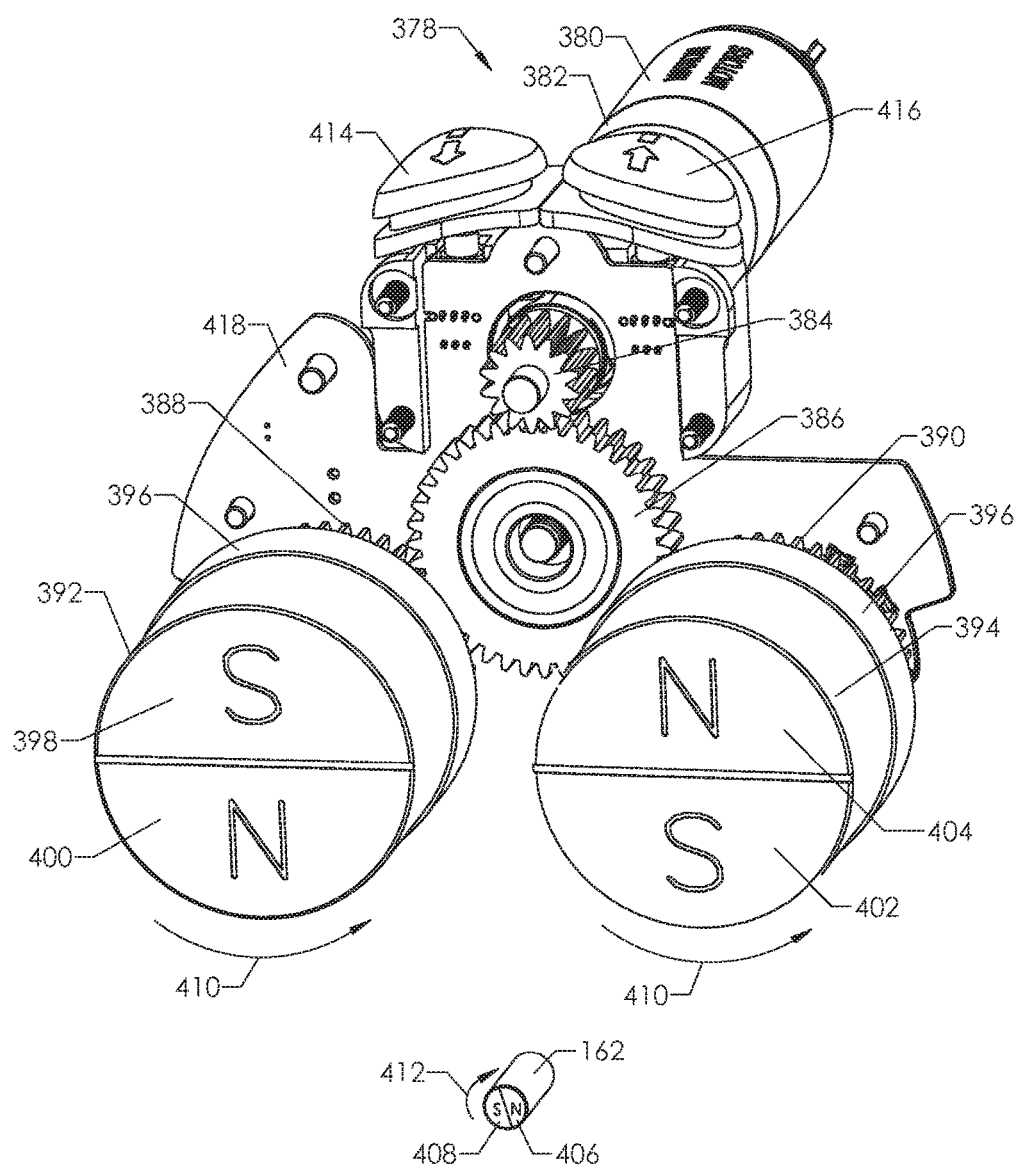
FIG. 22 illustrates internal components of an external adjustment device for non-invasively adjusting an intramedullary bone transport device according to one embodiment.
Figure 23:
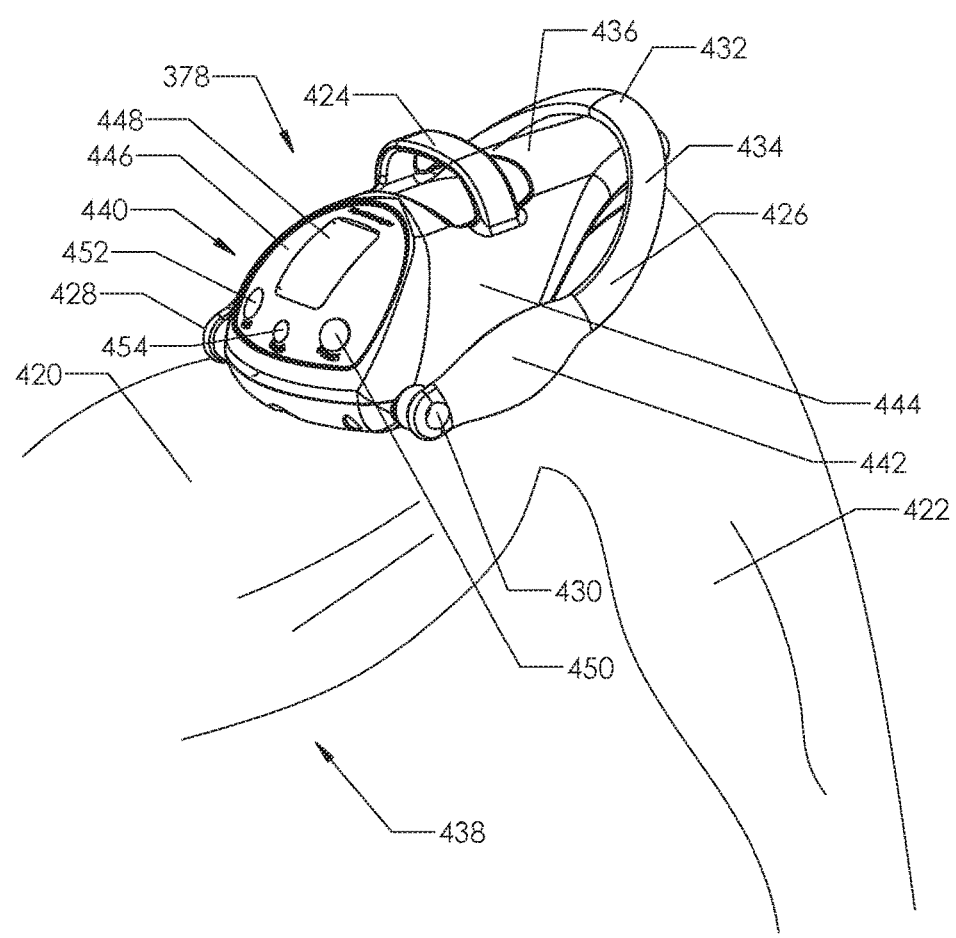
FIG. 23 illustrates an external adjustment device in a configuration for adjusting an intramedullary bone transport device implanted within the femur.
Figure 24:
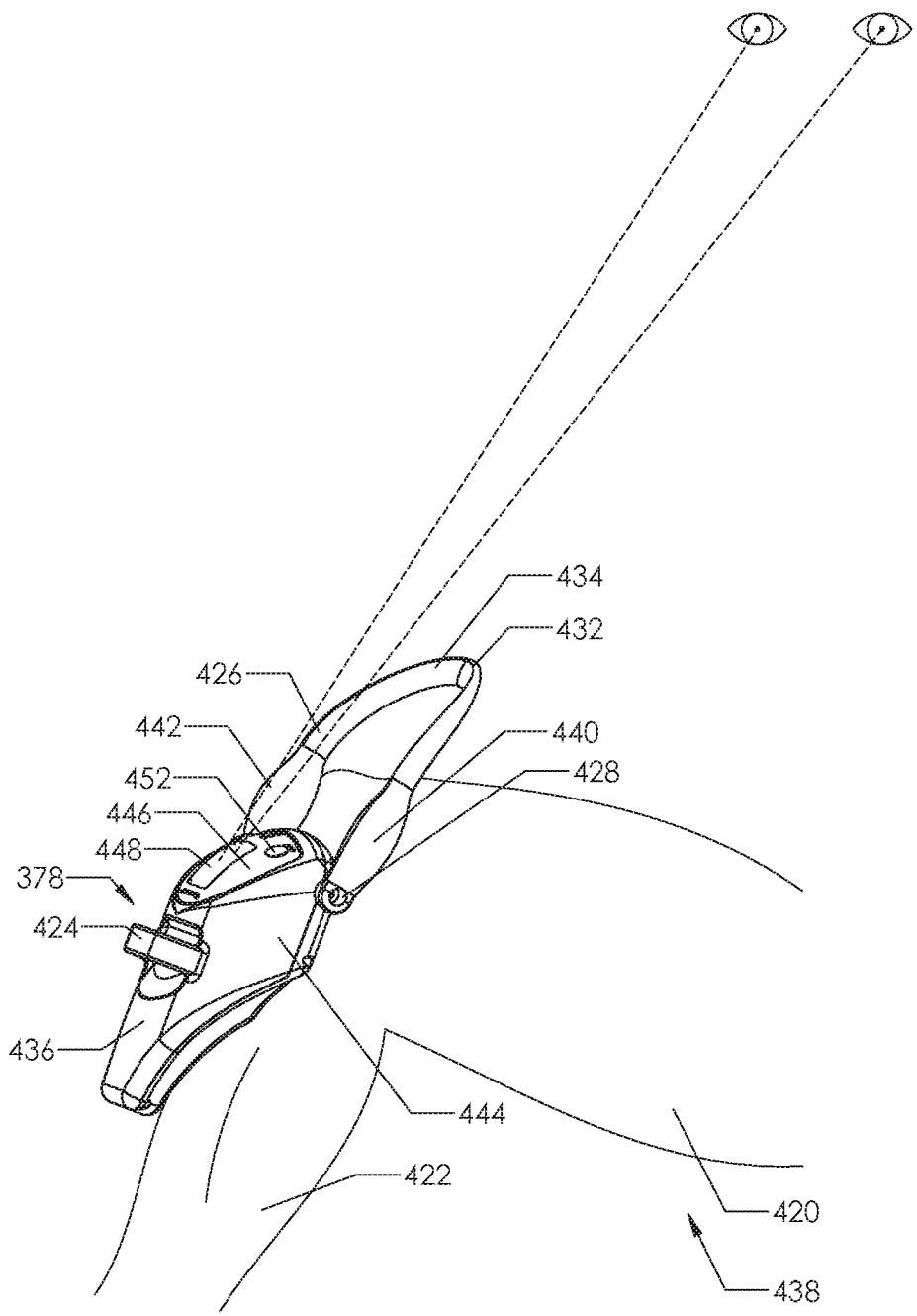
FIG. 24 illustrates an external adjustment device in a configuration for adjusting an intramedullary bone transport device implanted within the tibia.

FIGS. 22-24 illustrate an external adjustment device 378 configured for applying a moving magnetic field to allow for non-invasive adjustment of the bone transport device 100, 318, 336, 356 by turning a permanent magnet 162 within the bone transport device 100, 318, 336, 356, as described. FIG. 22 illustrates the internal components of the external adjustment device 378, and for clear reference, shows the permanent magnet 162 of the bone transport device 100, 318, 336, 356, without the rest of the assembly. The internal working components of the external adjustment device 378 may, in certain embodiments, be similar to that described in U.S. Patent Application Publication No. 2012/0004494, which is incorporated by reference herein. A motor 380 with a gear box 382 outputs to a motor gear 384. Motor gear 384 engages and turns central (idler) gear 386, which has the appropriate number of teeth to turn first and second magnet gears 388, 390 at identical rotational speeds. First and second magnets 392, 394 turn in unison with first and second magnet gears 388, 390, respectively. Each magnet 392, 394 is held within a respective magnet cup 396 (shown partially). An exemplary rotational speed is 60 RPM or less. This speed range may be desired in order to limit the amount of current density induced in the body tissue and fluids, to meet international guidelines or standards. As seen in FIG. 22, the south pole 398 of the first magnet 392 is oriented the same as the north pole 404 of the second magnet 394, and likewise, the first magnet 392 has its north pole 400 oriented the same as the south pole 402 of the second magnet 394. As these two magnets 392, 394 turn synchronously together, they apply a complementary and additive moving magnetic field to the radially-poled, permanent magnet 162, having a north pole 406 and a south pole 408. Magnets having multiple north poles (for example, two) and multiple south poles (for example, two) are also contemplated in each of the devices. As the two magnets 392, 394 turn in a first rotational direction 410 (e.g., counter-clockwise), the magnetic coupling causes the permanent magnet 162 to turn in a second, opposite rotational direction 412 (e.g., clockwise). The rotational direction of the motor 380 and corresponding rotational direction of the magnets 392, 394 is controlled by buttons 414, 416. One or more circuit boards 418 contain control circuitry for both sensing rotation of the magnets 392, 394 and controlling the rotation of the magnets 392, 394.

FIGS. 23 and 24 show the external adjustment device 378 for use with a bone transport device 100, 318, 336, 356 placed in the femur (FIG. 23) or the tibia (FIG. 24). The external adjustment device 378 has a first handle 424 for carrying or for steadying the external adjustment device 378, for example, steadying it against an upper leg 420, as in FIG. 23. An adjustable handle 426 is rotationally attached to the external adjustment device 378 at pivot points 428, 430. Pivot points 428, 430 have easily lockable/unlockable mechanisms, such as a spring loaded brake, ratchet or tightening screw, so that a desired angulation of the adjustable handle 426 in relation to housing 436 can be adjusted and locked in orientation. Adjustable handle 426 is shown in two different positions in FIGS. 23 and 24. In FIG. 23, adjustable handle 426 is set so that apex 432 of loop 434 rests against housing 436. In this position, patient 438 is able to hold onto one or both of grips 440, 442 while the adjustment procedure (for example transporting bone between 0.10 mm to 1.50 mm) is taking place. It is contemplated that the procedure could also be a lengthening procedure for an intramedullary bone lengthening device or a lengthening procedure for a lengthening plate which is attached external to the bone. Turning to FIG. 24, when the bone transport device 100, 318, 336, 356 is implanted in a tibia, the adjustable handle 426 may be changed to a position in which the patient 438 can grip onto the apex 432 so that the magnet area 444 of the external adjustment device 378 is held over the portion the bone transport device 100, 318, 336, 356 containing the permanent magnet 162. In both cases, patient is able to clearly view control panel 446 including a display 448. In a different configuration from the two directional buttons 414, 416 in FIG. 22, control panel 446 includes a start button 450, a stop button 452 and a mode button 454. Control circuitry contained on circuit boards 418 may be used by the surgeon to store important information related to the specific aspects of each particular patient. For example, in some patients an implant may be placed antegrade into the tibia. In other patients the implant may be placed either antegrade or retrograde into the femur. In each of these three cases, it may be desired to transport the bone either from distal to proximal or from proximal to distal. There are thus six (6) different scenarios. By having the ability to store information of this sort that is specific to each particular patient within the external adjustment device 378, the external adjustment device 378 can be configured to direct the magnets 392, 394 to turn in the correct direction automatically, while the patient need only place the external adjustment device 378 at the desired position, and push the start button 450. The information of the maximum allowable bone transport length per day and maximum allowable bone transport length per session can also be input and stored by the surgeon for safety purposes. These may also be added via an SD card or USB device, or by wireless input. An additional feature is a camera at the portion of the external adjustment device 378 that is placed over the skin. For example, the camera may be located between first magnet 392 and second magnet 394. The skin directly over the implanted permanent magnet 162 may be marked with indelible ink. A live image from the camera is then displayed on the display 448 of the control panel 446, allowing the user to place the first and second magnets 392, 394 directly over the area marked on the skin. Crosshairs can be overlayed on the display 448 over the live image, allowing the user to align the mark on the skin between the crosshairs, and thus optimally place the external adjustment device 378.

FIGS. 27 and 28 illustrate an alternative embodiment to the anti-jamming end stop described in FIGS. 2-4 and in FIG. 10. Transport sled 152 has been removed so that the rest of the anti-jamming assembly 482 can clearly be seen. Internal nut 456 is similar to internal nut 156 of FIGS. 2-4, 10 in that it can be made, simply as an internal thread of the transport tube 154, or alternatively, it can be a separate component. For example, the outer surface of the internal nut 456 may be made with an external thread 458 and the inner surface of the transport tube 154 may be made with a mating internal thread. These two surfaces may be bonded to each other, with adhesives, epoxies, etc., so that the internal thread of the internal nut 456 mates with the external threads 161 of the lead screw 160. In FIG. 27, a single pawl ring 460, having a single pawl 462 is secured to the lead screw 160 by welding, adhesive, epoxy or other methods. The single pawl 462 thus turns in unison with the lead screw 160. The end of the internal nut 456 has a ledge 470 at its end. This ledge 470 is configured to abut the single pawl 462 when the lead screw 160 reaches the end of its desired travel in relation to the internal nut 456. In FIG. 27, there are several turns remaining in the travel of the lead screw 160. In FIG. 28, the lead screw has reached the end of its desired travel and the single pawl 462 now abuts the ledge 470, thus not allowing any more rotation in this direction for the lead screw 160. The opposing forces between the single pawl 462 and the ledge 470 assure that the internal threads of the internal nut 456 will not jam with the external threads 161 of the lead screw 160. Another single pawl 480 at the opposite end of the internal nut 456 may be used to engage with another ledge (not shown) at the opposite end of the lead screw 160, thus eliminating jamming at the opposite end of travel of the internal nut 456 and lead screw 160.

FIGS. 29 and 30 show an alternative anti-jamming assembly 484 to the embodiment of FIGS. 27 and 28. In FIG. 29, the end piece 472 of the lead screw 160 has multiple pawls 474, which engage multiple ledges or teeth 478 when lead screw 160 reaches the end of its travel. The stress between the pawl and ledge is now distributed amongst multiple pawls 474 and ledges or teeth 478, thus also allowing a smaller axial dimension of the pawls 474 and ledges 478.

Returning to FIGS. 5 and 6, a bone transport procedure is described. After patient is prepped for surgery, a drill entry point 131 is chosen to ream a hole in the medullary canal of the tibia 136. Intramedullary bone transport device 100 is inserted into reamed medullary canal and secured with bone screws 126, 128, 130, 132, 134. Prior to creating an osteotomy 147, bone segment 144 for transport is chosen and secured to transport sled 152 with screw assemblies 112 as described herein. Osteotomy 147 is then made, freeing bone segment 144 from proximal portion of tibia 138. Osteotomy 147 may be made with osteotomes or a Gigli saw. As an alternative, the osteotomy 147 may be made prior to securing the bone segment 144 to the transport sled 152. Prior to recovering the patient, a test transport procedure may be performed in the operating theater, for example using an external adjustment device 378 covered with a sterile drape. This test transport procedure may be done either to confirm that the intramedullary bone transport device 100 has not been damaged by the insertion procedure or to set the osteotomy 147 at a desired initial gap distance, for example zero (0) to five (5.0) mm. The patient is then recovered, and within the first week after surgery, non-invasive bone transport procedures are initiated by the physician, patient or family or friend of patient, typically consisting of transporting about 1 mm per day. For example 1 mm, once per day, or 0.5 mm, twice per day, 0.33 mm, three times per day, etc. using the external adjustment device 378 as in FIGS. 23 and 24. As the bone segment 144 transports, new bone 153 begins to form where the missing portion 142 had previously been. Towards the end of the patient's transport period of treatment, the bone segment 144 nears the proximal end 135 of the distal portion 140 of the tibia 136. (All procedures described may be done on a variety of different bones.) A final gap 151 may be decided upon by the physician, and when this final gap 151 is reached (for example, 5 mm), the surgeon may desire to do a grafting procedure to facilitate the continuity of bone between the bone segment 144 and the distal portion 140 of the tibia 136. The new bone 153 is typically allowed approximately one month per 10 mm of transported length to consolidate, but this time period can vary greatly depending upon the biological characteristic (e.g. diabetes) and habits (e.g. smoking) of the patient.

Figure 31A:
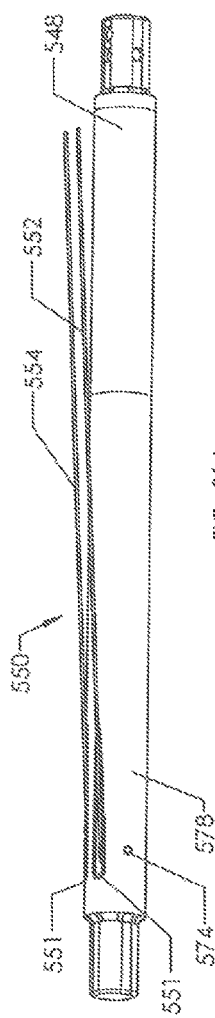
FIG. 31A illustrates an intramedullary bone transport device having a reverse block and tackle arrangement.
Figure 31B:
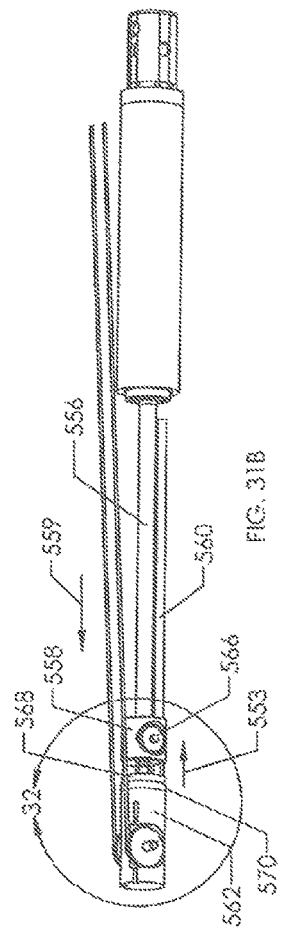
FIG. 31B illustrates the intramedullary bone transport device of FIG. 31A with a portion of the housing removed.
Figure 32:
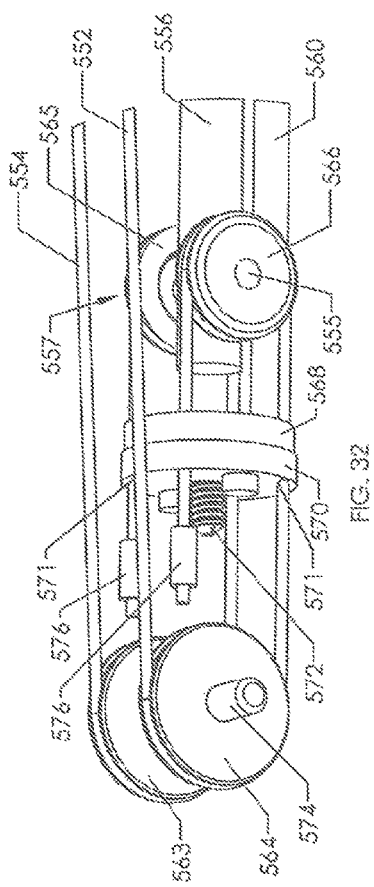
FIG. 32 illustrates detail 32 of FIG. 31B with portions removed for clarity.

FIG. 31A illustrates an intramedullary bone transport device 550 having a reverse block and tackle arrangement according to another embodiment. A first housing portion 578 and a second housing portion 548 enclose the internal reverse block and tackle components, shown in FIGS. 31B and 32. First housing portion 578 contains two slits 551 through which first tension line 552 and second tension line 554 exit. After implantation, bone segment 144 is secured to tension lines 552, 554 using bone screws having a clamp feature at their tips that enters the intramedullary canal and grips each of the tension lines 552, 554. The lead screw 556 is turned by permanent magnet 162 and gear stages 180, 182, 184 as in other embodiments. The nut 558 moves along lead screw 556 in first direction 553 as lead screw 556 is turned. The tension lines 552, 554 wrap around nut pulleys 566, 565 respectively (shown without nut 558 in FIG. 32). The nut pulleys 566, 565 are held rotatably to the nut 558 by pins 555, 557. The exit pulleys 563, 564 are held rotatably to the wire seal block 562 and first housing portion 578 with axle pin 574, which may be welded to the first housing portion 578 at each end. The tension lines 552, 554 wrap around exit pulleys 564, 563 respectively. At the end of tension lines 552, 554 are crimped lugs 576, which are secured axially within cavities in the wire seal block 562. A seal 570 is sandwiched between the wire seal block 562 and a seal support plate 568 by screw 572. The four (4) inner diameters 571 passing through the seal 570 are sized to be slightly smaller than the outer diameter of the tension lines 552, 554, so that any body fluids entering through slits 551 cannot enter further into the section of first housing portion 578 and second housing portion 548 containing lead screw 556, nut 558, permanent magnet 162 and gear stages 180, 182, 184. The seal 570 is made from an elastomer such as EPDM, so that tension lines 552, 554 may move through inner diameters 571 while still maintaining a sealed condition. In FIG. 32, the nut 558 and the wire seal block 562 are not shown so that more detail of the pathway of the tension lines 552, 554 may be seen. A guide rod 560 is secured to the assembly of the wire seal block 562, seal 570, and seal support plate 568. The nut 558 has an off center guide hole sized for sliding over the guide rod 560. As the nut 558 moves in first direction 553 over turning lead screw 556, nut pulleys 566, 565 move along with nut 558, causing each tension line 552, 554 to be pulled around exit pulleys 564, 563, thus allowing tension lines 552, 554 to pull bone segment 144 in second direction 559. Because of the reverse block and tackle arrangement, the tension lines 552, 554 move at a axial rate that is twice as fast as the rate of axial movement rate of the nut 558. Thus, for a nut 558 that travels only 55 mm total travel over lead screw 556, the tension lines 552, 554 are each pulled for 110 mm total travel, allowing for a compact device which still produces a large amount of bone transport length capability.

FIGS. 33 through 36 illustrate an intramedullary bone transport device 528 according to another embodiment having a ribbon-driven transport sled 530. Lead screw 160 is driven by permanent magnet 162, with gear stages 180,182, 184 as in FIGS. 1-4, however, the connection between lead screw 160 and transport sled 530 is no longer direct. Nut 532 having internal threading is coupled to lead screw 160 and moves longitudinally as lead screw 160 turns. Ribbon 534 is secured to nut 532, for example by welding or crimping, at one end and to transport sled 530 at the other end. Pulley 536 is rotatably coupled to enclosed housing 546 via axle 538. Ribbon 534 extends around pulley 536 so that movement of nut 532 in first direction 540 pulls ribbon 534 around pulley 536, causing transport sled to move in second direction 542. The multiple types of dynamic covers 320 described in prior embodiments, would also be usable in this embodiment. The ribbon in FIGS. 33-36 is a single material ribbon made from Nitinol or stainless steel, for example 0.006" thick Nitinol ribbon. As yet a further embodiment, ribbon 534 may be constructed of a laminate of several ribbon layers bonded together, for example four layers of 0.002" thick Nitinol or three layers of 0.003" thick Nitinol. The layers are bonded together with a flexible adhesive, such as a urethane adhesive, which allows the layers to slide slightly in longitudinal relation to each other, as they move around the pulley 536. Each of the layers may be a single ribbon structure as described, or may also be a multifilar, woven ribbon. The laminate construction allows for a nut 532 that not only can pull transport sled 530, but also push transport sled 530, due to the increased column stiffness during compression. When this push/pull embodiments is in push mode, radii 544 (as seen in FIG. 35) in the inner walls of enclosed housing 546 serve as a path for the ribbon 534 when the ribbon 534 is in compression (pushing). Ribbon 534 can refer to any analogous tensile member, for example one or more wires or cables configured to extend around pulley 536.

Other alternatives exist for constructing any of the embodiments presented herein. As one example, instead of solid rare earth magnet material, the magnets presented may be made as composite rare earth magnets, such as those described in U.S. Patent Application Publication Nos. 2011/0057756, 2012/0019341, and 2012/0019342, which are incorporated by reference herein.

A maintenance feature, such as a magnetic plate, may be incorporated on any of the embodiments of the implant devices presented herein, such as those described in U.S. Patent Application Publication No. 2012/0035661.

While embodiments of the present invention have been shown and described, various modifications may be made without departing from the scope of the present invention. The invention, therefore, should not be limited, except to the following claims, and their equivalents.

What is claimed is:

1. An implantable dynamic apparatus comprising:
 a nail having a first portion and a second portion, the first portion of the nail configured for securing to a first portion of bone, the second portion of the nail configured for securing to a second portion of bone;
 the second portion of the nail configured to be longitudinally moveable with respect to the first portion of the nail, wherein the second portion of the nail includes an internally threaded feature;
 a magnetic assembly configured to be non-invasively actuated by a moving magnetic field;
 a lead screw having an externally threaded portion, the lead screw coupled to the magnetic assembly, wherein the externally threaded portion of the lead screw engages the internally threaded feature of the second portion of the nail;
 wherein actuation of the magnetic assembly turns the lead screw, which in turn changes the longitudinal displacement between the first portion of the nail and the second portion of the nail;
 a first abutment surface coupled to the lead screw;
 a second abutment surface coupled to the second portion of the nail; and
 wherein the turning of the lead screw in a first direction causes the first abutment surface to contact the second abutment surface, stopping the motion of the lead screw with respect to the second portion of the nail, and wherein subsequent turning of the nail in a second direction is not impeded by any jamming between the internally threaded feature and the externally threaded portion.

* * * * *